(12) United States Patent
Van der Poll et al.

(10) Patent No.: US 11,839,605 B2
(45) Date of Patent: Dec. 12, 2023

(54) NON-INJECTABLE HYDROGEL FORMULATIONS FOR SMART RELEASE

(71) Applicant: Alivio Therapeutics, Inc., Boston, MA (US)

(72) Inventors: Derek G. Van der Poll, Medford, MA (US); Dominick J. Blasioli, Chelmsford, MA (US); Gregory T. Zugates, Chelmsford, MA (US)

(73) Assignee: Alivio Therapeutics, Inc., Boston, MA (US)

( * ) Notice: Subject to any disclaimer, the term of this patent is extended or adjusted under 35 U.S.C. 154(b) by 0 days.

(21) Appl. No.: 16/566,414

(22) Filed: Sep. 10, 2019

(65) Prior Publication Data

US 2020/0114010 A1    Apr. 16, 2020

Related U.S. Application Data

(60) Provisional application No. 62/744,489, filed on Oct. 11, 2018.

(51) Int. Cl.
*A61K 31/436* (2006.01)
*A61K 9/00* (2006.01)
(Continued)

(52) U.S. Cl.
CPC .......... *A61K 31/436* (2013.01); *A61K 9/0053* (2013.01); *A61K 9/02* (2013.01);
(Continued)

(58) Field of Classification Search
None
See application file for complete search history.

(56) References Cited

U.S. PATENT DOCUMENTS

| 4,027,038 A | 5/1977 | Bernstein |
| 6,031,017 A | 2/2000 | Waki |

(Continued)

FOREIGN PATENT DOCUMENTS

| AU | 2015200633 | 2/2015 |
| CN | 103479600 A | 1/2014 |

(Continued)

OTHER PUBLICATIONS

Li et al., "Role of interleukin-22 in inflammatory bowel disease", World J. Gastroenterol., 20(48): 18177-18188 (Year: 2014).*

(Continued)

*Primary Examiner* — Bethany P Barham
*Assistant Examiner* — Barbara S Frazier
(74) *Attorney, Agent, or Firm* — WOMBLE BOND DICKINSON (US) LLP; Danielle L. Herritt; Mark R. DeLuca

(57) ABSTRACT

A non-injectable formulation or formulation for instillation, including self-assembling hydrogels formed of gelators such as the Food and Drug Administration's Generally Regarded as Safe (GRAS) compounds like ascorbyl palmitate, in the form of capsules, tablets, oral suspensions, enemas, and rectal or vaginal suppositories or inserts have been developed. In a preferred embodiment, the formulation contains anti-inflammatories, anti-infectives, or other therapeutic, prophylactic, or diagnostic agents that can be administered orally, especially when lower blood levels relative to tissue levels of agent are preferred. In the most preferred formulation, the composition contains tacrolimus-loaded ascorbyl palmitate gel microfibers containing nanostructures ("hydrogels").

15 Claims, 5 Drawing Sheets

(51) Int. Cl.
| | |
|---|---|
| *A61K 9/02* | (2006.01) |
| *A61K 9/19* | (2006.01) |
| *A61K 39/00* | (2006.01) |
| *A61K 47/22* | (2006.01) |
| *A61K 47/36* | (2006.01) |
| *A61P 37/02* | (2006.01) |
| *A61P 37/06* | (2006.01) |
| *A61K 45/06* | (2006.01) |

(52) U.S. Cl.
CPC .......... *A61K 9/19* (2013.01); *A61K 39/00114* (2018.08); *A61K 47/22* (2013.01); *A61K 47/36* (2013.01); *A61P 37/02* (2018.01); *A61P 37/06* (2018.01); *A61K 45/06* (2013.01)

(56) References Cited

U.S. PATENT DOCUMENTS

| | | |
|---|---|---|
| 6,471,970 B1 | 10/2002 | Fanara |
| 9,452,178 B1 | 9/2016 | Hauser |
| 9,962,339 B2 | 5/2018 | Karp |
| 9,974,859 B2 | 5/2018 | Karp |
| 10,300,023 B1 | 5/2019 | Karp |
| 10,568,840 B2 | 2/2020 | Karp |
| 11,020,410 B2 | 6/2021 | Karp |
| 2003/0199477 A1 | 10/2003 | Fanara |
| 2005/0084470 A1 | 4/2005 | Abbas |
| 2005/0220822 A1 | 10/2005 | Hoffman |
| 2005/0267036 A1 | 12/2005 | Garry |
| 2005/0287198 A1 | 12/2005 | Murthy |
| 2007/0009926 A1* | 1/2007 | Veas .................. A61P 31/00 435/5 |
| 2007/0243589 A1 | 10/2007 | Gill et al. |
| 2008/0004398 A1 | 1/2008 | Durrieu |
| 2008/0021068 A1 | 1/2008 | Alam |
| 2008/0038316 A1 | 2/2008 | Wong |
| 2009/0048296 A1 | 2/2009 | Campbell |
| 2009/0110735 A1 | 4/2009 | Maggio |
| 2009/0257968 A1 | 10/2009 | Walton |
| 2009/0263489 A1 | 10/2009 | Zanella |
| 2012/0022158 A1 | 1/2012 | Niu |
| 2012/0189588 A1 | 7/2012 | Nahas |
| 2012/0251536 A1 | 10/2012 | Mainwaring |
| 2013/0079371 A1 | 3/2013 | Sundberg |
| 2013/0273140 A1 | 10/2013 | Maggio |
| 2013/0280334 A1 | 10/2013 | Karp |
| 2013/0309286 A1 | 11/2013 | Rolf |
| 2014/0302144 A1 | 10/2014 | Koutsopoulos |
| 2015/0018387 A1 | 1/2015 | Campbell |
| 2015/0125403 A1 | 5/2015 | Joerger |
| 2015/0202586 A1 | 7/2015 | Imoto |
| 2015/0297731 A1 | 10/2015 | Chiou |
| 2016/0243026 A1 | 8/2016 | Pathak |
| 2017/0000888 A1 | 1/2017 | Karp |
| 2017/0035891 A1 | 2/2017 | Karp |
| 2017/0100342 A1 | 4/2017 | Karp |
| 2017/0319500 A1 | 11/2017 | Karp |
| 2018/0050055 A1 | 2/2018 | Ahmed |
| 2018/0184649 A1 | 7/2018 | Harel et al. |

FOREIGN PATENT DOCUMENTS

| | | |
|---|---|---|
| EP | 0517211 | 6/1992 |
| EP | 1063007 | 12/2000 |
| EP | 2361640 | 2/2010 |
| FR | 2417494 | 9/1979 |
| WO | 9907416 | 2/1999 |
| WO | 2002006227 | 1/2002 |
| WO | 2003006043 | 1/2003 |
| WO | 2005056039 | 6/2005 |
| WO | 2006008386 | 1/2006 |
| WO | 2009097704 | 8/2009 |
| WO | 2010033726 | 3/2010 |
| WO | 2012040623 | 3/2012 |
| WO | 2014041378 | 3/2014 |
| WO | 2014089472 | 6/2014 |
| WO | 2014107566 | 7/2014 |
| WO | 2015075699 | 5/2015 |
| WO | 2017062818 | 4/2017 |
| WO | 2017193138 | 11/2017 |
| WO | 2017193139 | 11/2017 |
| WO | 2019195546 | 10/2019 |

OTHER PUBLICATIONS

Baumgart et al., "Rescue therapy with tacrolimus is effective in patients with sever and refractory inflammatory bowel disease", Aliment. Pharmacol. Ther., 17:1273-1281 (Year: 2003).*
Bhuniya, et al., "(S)-(+)-Ibuprofen-Based Hydrogelators: An Approach Toward Anti-Inflammatory Drug Delivery," Tetrahedron Lett. 47:7153-6 (2006).
Caran, et al., "Anatomy of a Gel. Amino Acid Derivatives that Rigidity Water at Submillimolar Concentrations,"Am. Chem. Soc., 122: 11679-11691 (2002).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Donati, et al., "Synergistic effects in semidilute mixed solutions of alginate and lactose-midified chitosan (chitlac)", Biomacromolecules, 8:957-62 (2007).
Gopinath, et al., "Ascorbyl palmitate vesicles (aspasomes): formation characterization and applications", Intl J Pharma., 271(1-2):95-113 (2004).
Han, et al., "Catalytic ester-amide exchange using group (iv) metal alkoxide-activator complexes", JACS, 127:10039-44 (2005).
Helmenstine, "Phosphate-Buffered Saline or PBS Solution", ThoughtCo., 1-4 (2018).
Higuchi, et al., "Specificity of Esterases and Effect of Structure of Prodrug Esters of Acylated Acetaminophen on Hydrolytic Reactivity", in: Pharmacokinetics, Benet et al. Eds (New York, Plenum Press, 1984), pp. 67-82.
Indomethacin, MSDS product information, copyright Jun. 19, 2012.
International Search Report for PCT application PCT/US2018/016835 dated Jul. 12, 2018.
International Search Report for PCT/US2016/056070 dated Jan. 12, 2017.
International Search Report for PCT/US2017/031614 dated Jul. 26, 2017.
International Search Report for PCT/US2017/031615 dated Sep. 25, 2017.
International Search Report for corresponding PCT application PCT/US2019/050405 dated Dec. 5, 2019.
International Search Report for PCT/US2018/031654 dated Aug. 8, 2018.
International Search Report PCTUS2019/025782 dated Jun. 26, 2019.
Kalgutkar, et al., "Ester and Amide Derivatives of the Nonsteriodal Antiinflammatory Drug,Indomethacin, as selective cyclooxygenase-2 inhibitors," J. Med. Chem.,43:2860-70 (2000).
Kameta, et al., "One-Dimensional Hollow Cylinder and Three-Dimensional Meshworls of supramoleular Nanotube Hyrdogels for Fixation of Proteins", Nanotechnology, 515-519 (2010).
Karim, et al., "Effectiveness and Safety of Tenofovir Gel, and Antiretroviral Microbicide, for the Prevention of HIV Infection in Women", Science, 329:1168-1174 (2010).
Kohane, et al., "A re-examination of tetrodotoxin for prolonged duration local anesthesia", Anesthesiology, 89(1):119-131 (1998).
Krog, et al., "Food Emulsifiers: Their Chemical and Physical Properties", Food Emulsions 4th Edition, 45FF, CRC Press (2004).
Kumar, et al., "First snapshot of a nonpolymeric hydrogelator interacting with its getting solvents", Chem. Commun., 4059-62 (2005).
Li, et al., Thermosensitive hydrogel of hydrophobically-modified methylcellulose for intravaginal drug delivery, J. Mater. Sci .: Mater. Med., 23:1913-1919 (2012).

(56) References Cited

OTHER PUBLICATIONS

Mahalingam, et al., "Design of a Semisolid Vaginal Microbicide Gel by Relating Composition to Properties and Performance", Pharm. Res., 27:2478-2491 (2010).

Marsich, et al., "Alginate/lactose-modified chitosan hydrogels: A bioactive biomaterial for chondrocyte encapsulation", J Biomat Mater Res A, 84(2):364-76 (2008).

Nishimura, et al., "Analysis of reducing end-groups produced by enzymatic scission of glycoside linkages in O-methylcellulose", Carbohydrate Res., 267:291-8 (1995).

Persico, et al., "Effect of tolmetin glycine amide (McN-4366) a prodrug of tolmetin sodium on adjuvant arthritis in the rat", J Pharma Exp Therap., 247(3):889-96 (1988).

Pietzyk, et al., "Degradation of phosphatidylcholine in liposomes containing carboplatin in dependence on composition and storage conditions", Intl J Pharma., 196(2):215-8 (2008).

Poulsen, et al., "Effect of topical vehicle composition on the in vitro release of fluocinolone acetonide and its acetate ester", J Pharma Sci., 57(6):928-33 (1968).

Rajabalaya, et al., "Studies on effect of plasticizer on invitro release and exvivo permeation from eudragit e100 based chlorpheniramine maleate matrix type transdermal delivery system", J Excipients Food Chem., 1(2):1-12 (2010).

Scogs, substances list, http://www.fda.gov/Food/IngredientsPackagingLabeling/GRAS/SCOGS/ucm084104. Retrieved from interner Apr. 3, 2014.

Szuts, et al., "Study of thermos-sensitive gel-forming properties of sucrose stearates", J Excipients Food Chem., 1(2):13-20 (2010).

Tomsic, et al., "Internally self-assembled thermoreversible gelling mulsions:ISAsomes in methylcellulose, k-carragrrnan, and mixed hydrogels", Langmuir, 25:9525 (2009).

Toth and Urtis, "Commonly used muscle relaxant therapies for acute low back pain: A review of carisoprodol cyclobenzaprine hydrochloride, and metaxalone", Clin Therap., 26(9):1355-67 (2004).

Ullrich, et al., "Sucrose ester nanodispersions: Microviscosity and viscoelastic properties", Eu J Pharma Biopharma., 70:550-5 (2008).

Valecillo, et al., "A liquid crystal of ascorbyl palmitate, used as a vaccine platform, provides sustained release of antigen and has intrinsic pro-infammtory and adjuvant actvities which are dependent on MyD88 adaptor protein", J. Cont. Release, 214:12-22 (2015).

Van Esch, et al., "New functional materials based om self-assembling organogels: from serendipity towards design", Angew Chem Int., 39:2263-66 (2000).

Vigroux, et al., "Cyclization-activated prodrugs: N-(substituted 2-hydroxyphenyl and 2-hydroxypropyl)carbamates based on ring-opened derivatives of active benzoxazolones and oxazolidinones as mutual prodrugs of acetaminophen", J Med Chem., 38:3983-94 (1995).

Vinson, et al., "Direct imaging of surfactant micelles, vesicles, discs, and ripple phase structures by cryo-transmission electron microscopy", Journal of Colloid Ans Interface Science, 142(1):74-91 (1991).

Vohra, et al., "Nanolipi carrier-based thermoreversible gel for localized delivery of docetaxel to breast cancer", Cancer Nanotechnol., 4(1-3):1-12 (2013).

Wang, et al., "Hydrogels as Separation Agents", Responsive Gels: Volume Transitions II, Advances in Polymer Science, 67-79 (1993).

Zhang, et al., "Self-assembled networks and molecular gels derived from long-chain, naturally-occurring fatty acids", J Brazilian Chem Soc., 27(2):239-55 (2016).

Zidan, et al., "Maximized Mucoadhesion and Skin Permeation of Anti-AIDS-Loaded Niosomal Gels", Pharmaceutics, Drug Delivery and Pharmaceutical Technology, 103:952-964 (2014).

Estroff, et al., "Water Gelation by Small Organic Molecules", Chem Rev., 104(3): 1201-1217 (2004).

Jibry, et al., "Amphiphilogels as drug carriers:effects of drug incorporation on the gel and on the active drug", Journal of Pharmacy and Pharmacology, 58(2):187-194 (2006).

Pal, et al., "Polymeric Hydrogels: Characterization and Biomedical Applications", Designed monomers and polymers, 12:197-220 (2009).

Sharma, et al., "Role of Polyfunctional Organic Molecules in the Synthesis and Assembly of Metal Nanoparticles", Journal of Nanoscience and Nanotechnology, 7(6): 2139-2150 (2007).

Tiwari, et al., "An enzyme-free highly glucose-specific assay using self-assembled aminobenzene boronic acid upon polyelectrolytes electrospun nanofibers-mat", Talanta, 82(5);1725-1732 (2010).

Van Bommel, et al., "Two-stage enzyme mediated drug release from LMWG hydrogels", Organic and Biomolecular Chemistry, 3(16): 2917-2920 (2005).

Yang, et al., "A simple visual assay based on small molecule hydrogels for detecting inhibitors of enzymes," Chem. Commun., 2424-25 (2004).

Docetaxel, C43H53NO14, Compound Summary, PubChem, pp. 1-74; https://pubchem.ncbi.nlm.nih.gov/compound/Docetaxel.

Tacrolimus, C44H69NO12, Compound Summary, PubChem, pp. 1-70, https://pubchem.ncbi.nlm.nih.gov/compound/445643.

* cited by examiner

NON-INJECTABLE HYDROGEL FORMULATIONS FOR SMART RELEASE

CROSS-REFERENCE TO RELATED APPLICATIONS

This application claims the benefit of and priority to U.S. Provisional Application No. 62/744,489 filed Oct. 11, 2018, which is hereby incorporated by reference in its entirety.

STATEMENT REGARDING FEDERALLY SPONSORED RESEARCH OR DEVELOPMENT

This invention was made with government support under W81XWH-20-1-0645 awarded by the U.S. Army Medical Research and Development Command. The government has certain rights in the invention.

FIELD OF THE INVENTION

This is generally in the field of oral controlled delivery of agents such as tacrolimus, from formulations based on a self-assembling hydrogel formed of self-assembled nanostructures, including oral suspensions, tablets, and capsules.

BACKGROUND OF THE INVENTION

Self-assembling gels which are stable in vivo for drug delivery are described in US2017/0000888. Self-assembly to form molecularly defined, high-ordered structures largely relies on non-covalent interactions. Structures formed from self-assembly are capable of entrapping molecules in solution during the assembly process. These can be administered in the form of gels, dried and rehydrated to form gels, or mechanically broken up into gel particles, which can be injected for delivery of hydrophobic and hydrophilic agents. Most self-assembled gels are formed from amphiphilic compounds which in theory may spontaneous assemble due to hydrophilic-hydrophobic interactions.

Heating in excess of 37-40° C. and/or addition of organic solvent is generally necessary to homogeneously disperse these amphiphilic agents in a medium, such that upon cooling, the amphiphilic agents assemble into ordered nano and micro structures, which can then form a self-supporting gel. The gel is useful for drug delivery, as a reservoir for controlled release of drug agents, and may possess desirable biochemical and mechanical properties as scaffold for tissue repair.

Although these gels are useful as depos for controlled drug delivery when administered by injection, it would be advantageous if an oral formulation could be provided. Oral formulations are easy to administer but have completely different pharmacokinetic and formulation issues than formulations for injection.

Therefore, it is an object of the present invention to provide a self-assembled gel composition and a process for loading agents therein to produce an oral formulation.

It is another object of the present invention to provide a self-assembled gel oral composition for delivery of agents such as tacrolimus where it is critical to control gastrointestinal absorption and avoid burst release which could lead to elevated blood levels causing toxicity or other side effects.

It is yet another object of the present invention to provide a self-assembled gel oral composition that maintains the activity of labile entrapped and/or encapsulated agents and provides extended controlled release.

It is a further object of the present invention to provide an oral formulation for administration as a capsule, tablet, or gel suspensions.

It is a further object of the present invention to provide a method for administration of a gel suspensions intra-rectally via enema, intra-vaginally, or as an instillation into the bladder.

SUMMARY OF THE INVENTION

Formulations containing particles of self-assembling hydrogels composed of gelators such as the Food and Drug Administration's Generally Regarded as Safe (GRAS) compounds like ascorbyl palmitate, and further processed into capsules, tablets, oral suspensions, enemas and rectal or vaginal suppositories or inserts, or suspensions for instillation, for delivery of therapeutic, prophylactic and/or diagnostic agents, have been developed. In a preferred embodiment, the formulation contains anti-inflammatories, anti-infectives, or other therapeutic and prophylactic agents that can be administered orally, especially when lower blood levels relative to tissue levels of the agent are preferred. In the most preferred formulation, the composition contains tacrolimus-loaded ascorbyl palmitate gel microfibers containing nanostructures ("hydrogels"). Tacrolimus is especially difficult to encapsulate in hydrogels due to its low solubility in water, requiring it first to be dissolved in an organic solvent such as methanol containing the gelator, then water added to the solution, then heated at an appropriate temperature to insure complete dissolution before cooling to form a drug-loaded hydrogel.

The therapeutic or prophylactic agent such as tacrolimus is incorporated into the hydrogels by first forming a homogenous solution of drug with a gelator such as ascorbyl palmitate. Typically, this organic solution is mixed with an aqueous phase and then heated to insure complete dissolution of both the drug and gelator. This solution forms a gel as it cools. The gel is then suspended into solution using mechanical agitation to form discrete drug-loaded hydrogel particles, which can be further washed with water or aqueous buffer to remove any residual drug or solvent. The particles can then be resuspended in an aqueous vehicle containing excipients to be used as an oral, rectal, vaginal, or bladder instilled formulation. Alternatively, the drug-loaded microfibers can be lyophilized, blended with excipients and then loaded into capsules or compressed into tablets, or formulated into suppositories for administration orally or rectally. In the most preferred embodiment, the loaded capsules or tablets are coated with an enteric polymer, or a polymer which is used to control or sustain release. A variety of excipients can be included to act as manufacturing aids, fillers, binders, distintegrants, or stabilizers.

In some embodiment, the weight percent of the agent compared to the total weight of the agent and the gelator in the gel or gel particles is between about 0.1% and about 30%, preferably between about 0.5% and about 15%, and most preferably between about 2% and about 12%. In some embodiments, the agent is tacrolimus, and optionally the gelator is ascorbyl palmitate.

In some embodiment, the weight percent of the gel particles in the tablet or capsule formulations (with excipients) is between about 2% and about 80%, preferably between about 5% and about 70%, and most preferably between about 10% and about 60%. In some embodiments, the excipients include sodium starch glycolate and mannitol.

The enteric-coated capsules filled with tacrolimus-loaded gel particles of this invention enable GI site-specific capsule dissolution and provide a means for controlled release of higher local tacrolimus levels in inflamed tissues but reduced systemic levels of tacrolimus in contrast to conventional tacrolimus formulations.

The formulations can be provided in the form of gels, lyophilized for administration in dried form which re-hydrate at the site of administration or which is hydrated for administration, disrupted into particles or dispersions, or co-administered with one or more additional therapeutic or prophylactic agents. In a preferred embodiment, the formulation is orally administered as a suspension of gel particles, or dried and loaded into an enteric-coated capsule or tablet, or as nanostructured hydrogels in the form of a suppository or insert. The benefit of the nanostructured gels in a capsule for oral delivery improves patient compliance and broadens the addressable patient population since the formulation can reach more parts of the GI tract, in contrast to the limited scope of enema formulations or injections, which are difficult to administer frequently and can only be used for certain parts of the body and gastrointestinal (GI) tract. The examples demonstrate that the formulation functions similarly when administered locally as a suspension of drug-loaded gel particles, or when dried and loaded into enteric-coated capsules for site specific GI delivery.

The self-assembled gel, its suspension formulation, or particle formulation, is administered to deliver an effective dosage of the therapeutic or prophylactic agent(s) to alleviate, prevent, or treat one or more symptoms of a disease or disorder. Administration can be orally, vaginally, rectally (enema), or as insert, or by instillation into a body lumen such as the bladder.

DETAILED DESCRIPTION OF THE INVENTION

I. Definitions

Figures 1A, 1B, 1C, 1D:
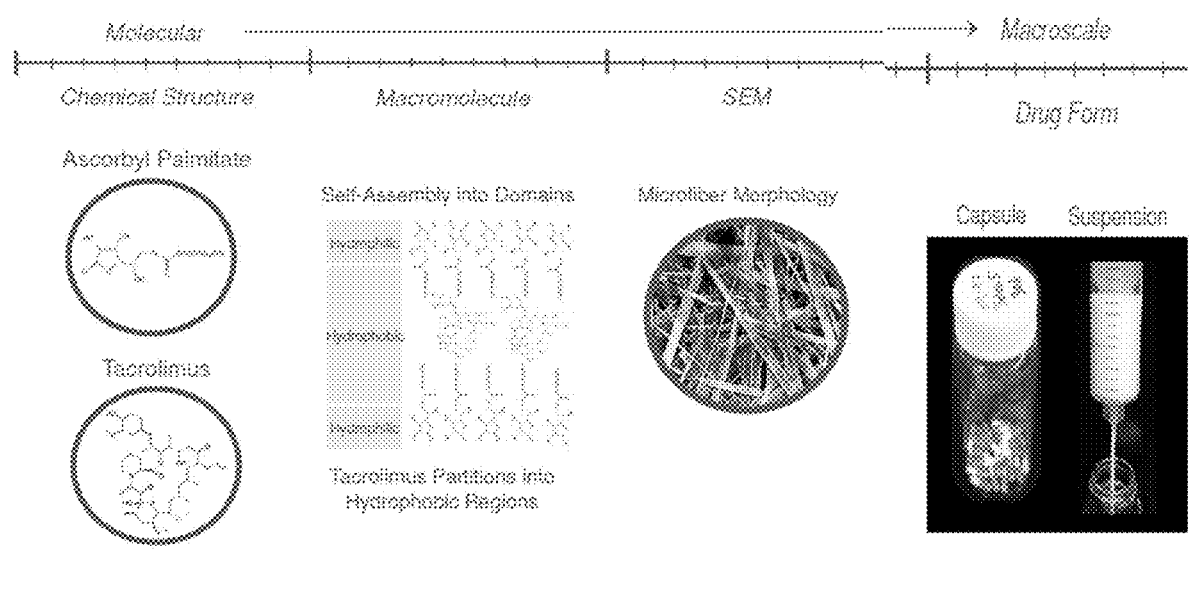
FIGS. 1A-1D is a schematic showing the chemical structures used to form macromolecules (1A), the self-assembled gels with drug (tacrolimus) partitioned into the hydrophobic regions of the gel. The gel exhibits a nano or microfiber morphology as shown by SEM (1B). The gel can be lyophilized, micronized (1C), and encapsulated into a gel capsule or resuspended into a liquid suspension for oral delivery (1D).

The term "gelators" refer to molecules that can self-assemble through non-covalent interactions, such as hydrogen-bonding, van der Waals interactions, hydrophobic interactions, ionic interactions, pi-pi stacking, or combinations thereof, in one or more solvents. Gelators can include hydrogelators (e.g., gelators that form hydrogels) and organo-gelators (e.g., gelators that form organo-gels). In some embodiments, gelators can form both hydrogels and organo-gels.

The term "self-assembling" refers to the capability of molecules to spontaneous assemble, or organize, to form a more highly ordered structure such as hydrogel in a suitable environment. As used herein, the gelators precipitate in solution under conditions wherein organized nanostructures are formed by non-covalent bonding between the gelator molecules, which are hydrated to form a hydrogel.

The term "hydrogel" refers to three-dimensional (3-D) networks of molecules covalently (e.g., polymeric hydrogels) or non-covalently (e.g., self-assembled hydrogels) held together where water is the major component. Gels can be formed via self-assembly of gelators or via chemical cross-linking of gelators. Water-based gelators can be used to form hydrogels.

The term "co-assembly", refers to the process of spontaneous assembly, or organization of at least two different types of molecules to form a more highly ordered structure such as hydrogel in a suitable environment, where molecules in the structure are generally organized in an ordered manner.

The term "organic solvent" refers to any carbon-containing substance that, in its liquid phase, is capable of dissolving a solid substance. Exemplary organic solvents commonly used in organic chemistry include toluene, tetrahydrofuran, acetone, dichloromethane, and hexane.

The term "water-miscible" refers to a solvent that mixes with water, in all proportions, to form a single homogenous liquid phase. This includes solvents like dimethyl sulfoxide (DMSO), tetrahydrofuran, acetone, ethanol, methanol, and dioxane, but generally excludes solvents such as hexane, oils, and ether. It also excludes solvents that have some, very limited miscibility or solubility in water such as ethyl acetate and dichloromethane, which are practically considered immiscible.

The term "percent (%) encapsulated" or "encapsulation percentage" is generally calculated as % encapsulated=weight of encapsulated agent(s)÷weight of total of initial agent(s)(encapsulated+unencapsulated)× 100%.

The term "encapsulation efficiency (EE)" is generally calculated as EE (%)=experimental/measured drug loading÷theoretical drug loading×100%.

Gel weight percent (w/v): Total mass of gelator(s) as a percentage of total solvent volume (i.e., organic solvent(s)+ water for hydrogels).

Drug loading efficiency (w/w): Mass of agent(s) as a percentage of total mass of gelator (amphiphile) and co-gelator, if present.

The term "pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration.

The terms "biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

The term "hydrophobic," as used herein, refers to the property of lacking affinity for or repelling water. For example, the more hydrophobic a polymer (or polymer segment), the more that polymer (or polymer segment) tends to not dissolve in, not mix with, or not be wetted by water.

The term "surfactant" as used herein refers to an agent that lowers the surface tension of a liquid.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

"Gastric resistant natural polymer", as used herein, refers to natural polymers or mixtures of natural polymers which are insoluble in the acidic pH of the stomach.

"Film-forming natural polymer", as used herein, refers to polymers useful for surface coatings that are applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches).

The term "therapeutic agent" refers to an agent that can be administered to prevent or treat one or more symptoms of a disease or disorder. Therapeutic agents can be nucleic acids or analogs thereof, a small molecule (molecular weight of less than 2000 Daltons, more typically less than 1000 Daltons), peptidomimetic, protein, or peptide, carbohydrate or sugar, lipid, or a combination thereof. In some embodiments, cells or cellular materials may be used as therapeutic agents.

The term "treating" or "preventing" a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder or condition includes ameliorating at least one symptom of the particular disease, disorder or condition, even if the underlying pathophysiology is not affected, such as treating the pain of a subject by administration of an analgesic agent even though such agent does not treat the cause of the pain.

The term "therapeutically effective amount" refers to an amount of a therapeutic or prophylactic agent, such as a biologic agent, that, when incorporated into and/or onto the self-assembled gel composition, produces some desired effect at a reasonable benefit/risk ratio applicable to any treatment. The effective amount may vary depending on such factors as the disease, disorder or condition being treated, the particular formulation being administered, the size of the subject, or the severity of the disease, disorder or condition.

The terms "incorporated," "encapsulated" and "entrapped" refers to incorporating and/or encapsulating and/or entrapping therapeutic or prophylactic agent(s) into in a gel composition or the nanostructures formed therein, regardless of the manner by which the therapeutic or prophylactic agent is incorporated, encapsulated, and/or entrapped.

"GRAS" is an acronym for the phrase Generally Recognized as Safe. Under sections 201(s) and 409 of the Federal Food, Drug, and Cosmetic Act (the Act), any substance that is intentionally added to food is a food additive, that is subject to premarket review and approval by FDA, unless the substance is generally recognized, among qualified experts, as having been adequately shown to be safe under the conditions of its intended use, or unless the use of the substance is otherwise excepted from the definition of a food additive. Under sections 201(s) and 409 of the Act, and FDA's implementing regulations in 21 CFR 170.3 and 21 CFR 170.30, the use of a food substance may be GRAS either through scientific procedures or, for a substance used in food before 1958, through experience based on common use in food under 21 CFR 170.30(b), general recognition of safety through scientific procedures requires the same quantity and quality of scientific evidence as is required to obtain approval of the substance as a food additive. General recognition of safety through scientific procedures is based upon the application of generally available and accepted scientific data, information, or methods, which ordinarily are published, as well as the application of scientific principles, and may be corroborated by the application of unpublished scientific data, information, or methods. The database of compounds meeting the requirements defined by 21 CFR is found in Title 21: Food and Drugs, Part 184.

Numerical ranges include, but are not limited to, ranges of temperatures, ranges of weight concentrations, ranges of molecular weights, ranges of integers, and ranges of times, etc. The ranges include sub-ranges and combinations of sub-ranges encompassed therein. Use of the term "about" is intended to describe values either above or below the stated value, which the term "about" modifies, in a range of approx. +/−10%; in other instances the values may range in value either above or below the stated value in a range of approx. +/−5%. When the term "about" is used before a range of numbers (i.e., about 1-5) or before a series of numbers (i.e., about 1, 2, 3, 4, etc.) it is intended to modify both ends of the range of numbers or each of the numbers in the series, unless specified otherwise.

II. Formulations

Self-Assembled Gel

FIG. 1 is a schematic showing the chemical structures used to form the self-assembled gels with drug (tacrolimus) partitioned into the hydrophobic regions of the gel. The gel consists of a nano or microfiber morphology as shown by SEM. The gel can be mechanically agitated to form drug-loaded gel particles that can be further processed to remove excess solvent and/or drug. The purified gel particles can then be resuspended in an appropriate vehicle containing excipients to form a gel suspension for oral, rectal, vaginal, or bladder delivery. Alternatively, the gel particles can be lyophilized and loaded into a capsule, compressed into a tablet, or resuspended into a liquid vehicle for oral delivery or other modes of administration as described below.

1. Gelators

Amphiphilic gelators, preferably those meeting the requirements for the U.S. Food and Drug Administration's list of Generally Required as Safe ("GRAS") (jointly referred to herein as "GRAS gelators"), which are suitable for self-assembly to form a gel are generally less than 2,500 Da, and may be enzyme-cleavable. The amphiphilic gelators self-assemble into gels formed from and including micro-/nano-structures (e.g., lamellar, micellar, vesicular, and/or fibrous structures).

In some embodiments, the amphiphilic gelators are ascorbyl alkanoate, sorbitan alkanoate, triglycerol monoalkanoate, sucrose alkanoate, glycocholic acid, or any combination thereof. In the preferred embodiments, the gelators are ascorbyl palmitate and ascorbyl stearate. The "ascorbyl" piece of the molecule is what imparts the inflammation targeting properties of the microfibers. Example 3 describes preparation of ascorbyl stearate microfiber suspensions as well as a comparison of ascorbyl palmitate (AP) and ascorbyl stearate (AS) gel sensitivity to lipase. Additional preferred gelators could include triglycerol monostearate, sorbitan monostearate, sorbitan monopalmitate, and sodium stearoyl lactylate.

The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can be ascorbyl palmitate, ascorbyl decanoate, ascorbyl laurate, ascorbyl caprylate, ascorbyl myristate, ascorbyl oleate, or any combination thereof. The sorbitan alkanoate can be sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof. Representative low molecular weight GRAS amphiphilic gelators include vitamin precursors such as ascorbyl palmitate (vitamin C precursor), retinyl acetate (vitamin A precursor), and alpha-tocopherol acetate (vitamin E precursor).

In some forms, an amphiphilic gelator is formed by synthetically conjugating one or more saturated or unsaturated hydrocarbon chains having $C_1$ to $C_{30}$ groups with a low molecular weight, generally hydrophilic compound, through esterification or a carbamate, anhydride, and/or amide linkage. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, etc., up to $C_{30}$ as wells as ranges falling within $C_1$ to $C_{30}$, for example, $C_1$ to $C_{29}$, $C_2$ to $C_{30}$, $C_3$ to $C_{28}$, etc.

In some embodiments, alpha tocopherol acetate, retinyl acetate, retinyl palmitate, or a combination thereof, can co-assemble with the gelators.

Typically, to form a viscous gel stable to inversion (e.g., resist flow when inverted at room temperature, approximately 25° C.), greater than 3%, 4%, 5% (wt/vol) or more gelators are completely dissolved in a liquid medium. The gels can include, independently, from about four, from about five, from about 10, or from about 15, to about 40 percent (to about 40, to about 30, to about 20, to about 15, to about 10, to five) of amphiphilic gelators by weight per volume.

In some forms, the self-assembled gel compositions include an enzyme-cleavable first gelator having a molecular weight of 2500 or less and a non-independent second gelator. Non-independent gelators do not form self-supporting gel at the concentration that would typically form self-supporting gel if combined with an enzyme-cleavable gelator. Exemplary non-independent second gelators include alpha tocopherol acetate, retinyl acetate, and retinyl palmitate. The non-independent gelators co-assemble with the first gelators to form the self-assembled gels.

The gels can include, independently, from about three to a maximum of 30-40 percent, more preferably about 4% to 10% by weight gelator per volume of gel. Above 30-40% the gel will begin to precipitate out of solution or become less injectable.

2. Gelation Medium

The liquid medium for the gelators to form self-assembled gel generally includes an aqueous solution or a two-solvent system of an organic solvent and water (or an aqueous buffer or salt solution) or an aqueous-organic mixture solvent system. Following gelation the organic solvent(s) are removed entirely or substantially removed (i.e., less than about 5%, 4%, 3%, 2%, 1%, 0.5%, or 0.1% or less of organic solvent(s) by weight in the resulting gel).

In one embodiment, a gelator is mixed and/or dissolved to homogeneity in an aqueous solution, preferably with strong mechanical mixing and/or heating. In another embodiment, a co-solvent medium including both water (or an aqueous buffer or salt solution) and a water-miscible organic solvent, is used to form a gelation solution.

Alternatively, the gelator can be dissolved initially in an organic solvent to form a solution with the gelator as the solute (termed "gelator solution") and water (or an aqueous buffer or salt solution) can be added subsequently to form the gelation medium.

Organic solvent(s) used in the gelation medium can be selected based on the solubility of gelators therein, its polarity, hydrophobicity, water-miscibility, and in some cases the acidity. Suitable organic solvents include water-miscible solvent or solvent that has an appreciable water solubility (e.g., greater than 5 g/100 g water), e.g., DMSO, dipropylene glycol, propylene glycol, hexyl butyrate, glycerol, acetone, dimethylformamide (DMF), tetrahydrofuran, dioxane, acetonitrile, alcohol such as ethanol, methanol or isopropyl alcohol, as well as low molecular weight polyethylene glycol (e.g., 1 kDa PEG which melts at 37° C.). In other forms, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, N,N'-dimethyl formamide, ethanol, isopropyl alcohol, butyl alcohol, pentyl alcohol, tetrahydrofuran, xylene, mesitylene, and/or any combination thereof. Organic solvents for gelation include dimethyl sulfoxide (DMSO), dipropylene glycol, propylene glycol, hexyl butyrate, glycerol, acetone, dimethylformamide, tetrahydrofuran, dioxane, acetonitrile, ethanol, and methanol. Fatty alcohols or long-chain alcohols may also be used. They are usually high-molecular-weight, straight-chain primary alcohols, but can also range from as few as 4-6 carbons to as many as 22-26, derived from natural fats and oils. Some commercially important fatty alcohols are lauryl, stearyl, and oleyl alcohols. Some are unsaturated and some are branched.

The aqueous solvent is typically water which may be sterilized and selected from distilled water, de-ionized water, pure or ultrapure water. In some instances, the aqueous solvent is an aqueous solution such as saline or other physiologically acceptable aqueous solutions containing salts and/or buffers, such as phosphate buffered saline (PBS), Ringer's solution, and isotonic sodium chloride, or any other aqueous solution acceptable for administration to a subject, such as an animal or human. The amounts of the aqueous solvent, such as water, is typically based on the amounts of the organic solvent used wherein the selected total volume or weight percentage of organic solvent(s) determined the volume or weight percentage of the water or aqueous solution (e.g., if 30 v/v % of organic solvent then 70 v/v % water).

In some instances, the amount of an organic solvent is no more than 1:1, 1:2, 1:3, 1:4, 1:5, 1:6, 1:7, 1:8, 1:9, 1:10, or less in volume compared to the volume of an aqueous solution (e.g., water, aqueous buffer, aqueous salt solution, optionally containing one or more additional agents). That is, the volume amount of the organic solvent in the total amount of liquid as used in forming a homogenous gel is generally less than about 50%, 33%, 25%, 20%, 17%, 14%, 12.5%, 11%, 10%, or 9%, and significantly less, typically less than 1%, for particles.

Gelation may require heating the gelation medium to temperatures ranging about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some instances, no heating is needed, or, if necessary, heating to about body temperature (37° C.) generates a homogeneous self-supporting gel that is stable to inversion. In other embodiments, the gelation medium is heated to complete dissolution, followed by cooling to about 37° C. or room temperature around 20-25° C.

Gelation can take place with or without heating. When heated, gelation can take place as the heated gelation solution is cooled. Leaving the gel on a stable surface for about one to two hours at room temperature results in a consistent self-supporting gel. Self-supporting gel comprises orderly assembled micro- or nano-structures with minimal precipitates. This can be confirmed using optical or electron microscopy.

Gelators and solvents are selected at an appropriate gelator concentration and appropriate volume and ratio of the aqueous-organic mixture solvent system, or both, to form self-supporting gel. Preferably, the gelator solution should not solidify or precipitate before the addition of an aqueous solution. Increasing the amount of the organic solvent or reducing the concentration of gelators in the organic solvent may prevent solidification of the gelator solution. When the gelator solution (in an organic solvent) is mixed with the aqueous solution, a self-supporting gel stable to inversion is formed, (following heating if necessary), rather than flowable mass/aggregates.

Following formation of self-supporting gels, the organic solvent in the gel may be removed to a residual level suitable for pharmaceutical applications. One or more purification techniques such as dialysis, centrifugation, filtration, drying, solvent exchange, or lyophilization, can be used to remove organic solvent(s). Residual organic solvent is within the stated limit of pharmaceutical products by the U.S. Food and Drug Administration (FDA) or below the acceptance criteria by U.S. Pharmacopeia Convention and/or International Conference on Harmonization guidance. For example, dichloromethane is below 600 ppm, methanol below 3,000 ppm, chloroform below 60 ppm; and within the limit by GMP or other quality based requirements.

Micro- and/or Nano-Structures

The agents can be encapsulated within and/or between the nanostructures, can be non-covalently bonded to the nanostructures, or both.

The hydrophobic parts and the hydrophilic parts of the gelator molecules can interact to form nanostructures (lamellae, sheets, fibers, particles) of gelator molecules. The agents can insert into and form part of the nanostructures, being encapsulated and/or entrapped in the nanostructures of the gel, or both. In hydrogels, the hydrophobic portions of gelators are located in the inner regions of a given nanostructures, and hydrophilic portions are located at the outer surfaces of the nanostructure. The nanostructure can have a width of from about three (e.g., from about four) to about five (e.g., to about four) nanometers and a length of several microns or more (e.g., one micron, two microns, three microns, four microns, five microns, ten microns, twenty microns, or twenty five microns). Several tens or hundreds of lamellae can bundle together to form nanostructures, such as fibers and sheet-like structures.

In some embodiments, the nanostructures include nanoparticles, micelles, liposome vesicles, fibers, and/or sheets. In some embodiments, the nanostructures can have a minimum dimension of 2 nm or more (e.g., 50 nm or more, 100 nm or more, 150 nm or more, 200 nm or more, 250 nm or more, 300 nm or more, 350 nm or more) and/or 400 nm or less (e.g., 350 nm or less, 300 nm or less, 250 nm or less, 200 nm or less, 150 nm or less, 100 nm or less, or 500 nm or less). In some embodiments, the nanostructures (e.g., fibers, sheets) have a length and/or width of several microns (e.g., one micron, two microns, three microns, four microns, five microns, ten microns, twenty microns, or twenty five microns) or more. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of several microns or more (e.g., one micron, two microns, three microns, four microns, five microns, ten microns, twenty microns, or twenty-five microns).

Degradation (Cleavable Linkage)

Stimuli evoking release can be present due to the characteristics at the site of administration or where release is desired, for example, tumors or areas of infection. These may be conditions present in the blood or serum, or conditions present inside or outside the cells, tissue or organ. These are characterized by low pH and the presence of degradative enzymes. The gel compositions may be designed to disassemble only under conditions present in a disease state of a cell, tissue or organ, e.g., inflammation, thus allowing for release of an agent at targeted tissue and/or organ. This is an alternative or may be used in combination to gel erosion-mediated and passive diffusion-mediated release of agent.

This responsive release is based on linkages formed from degradable chemical bonds (or functional groups) and/or tunable non-covalent association forces (e.g., electrostatic forces, van der Waals, or hydrogen bonding forces). In some embodiments, these linkages are (1) degradable covalent linkage between the hydrophilic segment and the hydrophobic segment of an amphiphilic gelator, (2) positioned in a prodrug-type gelator, which upon cleavage releases an active drug, and/or (3) covalent linkage or non-covalent association forces between a gelator and a therapeutic agent. The cleavage or dissociation of these linkages result in (1) more rapid or greater release of the encapsulated or entrapped agents compared to passive diffusion-mediated release of agent; and/or (2) converts prodrug gelator into active drug for release.

Stimuli evoking release includes intrinsic environment in vivo and user-applied stimulation, for example, enzymes, pH, oxidation, temperature, irradiation, ultrasound, metal ions, electrical stimuli, or electromagnetic stimuli. A typical responsive linkage is cleavable through enzyme and/or hydrolysis, based on a chemical bond involving an ester, an amide, an anhydride, a thioester, and/or a carbamate. In some embodiments, phosphate-based linkages can be cleaved by phosphatases or esterase. In some embodiments, labile linkages are redox cleavable and are cleaved upon reduction or oxidation (e.g., —S—S—). In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature. This can allow use of lower dosages, because the agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

The gel compositions can be designed for controlled degradation at a site of delivery or after a period of time, based on the conditions at the site of administration. Compared to free agent in a solution, the encapsulated and/or entrapped agent releases from the self-assembled gel much slower, for example, less than 30% of encapsulated and/or entrapped agent is released in the first three days and less than 70% in seven days. In the presence of a stimulus such as an enzyme, self-assembled gel formed from a gelator with an enzyme-degradable linkage releases the agent more rapidly, compared to the gel in a medium lacking the enzyme.

3. Therapeutic, Prophylactic and/or Diagnostic Agents

Therapeutic, prophylactic and/or diagnostic agents may be physically entrapped, encapsulated, and/or non-covalently associated with the nanostructures. The agents may be covalently modified with one or more gelators, one or more stabilizers, or be used as a gelator. Alternatively, they are incorporated into the assembled, ordered lamellar, vesicular, and/or nanofibrous structures of the gel composition or positioned on the surface of the assembled structures.

In preferred embodiments, the agent(s) are physically entrapped, encapsulated, and/or non-covalently associated with the nanostructures of the self-assembled gels by forming the gels first. Suspending the gels in an aqueous medium, such as a buffer, where the gel is optionally first broken to form particles (i.e., nano- and/or microparticles) and then mixing the resulting gel particle suspension with a second suspension containing one or more therapeutic, prophylactic, and/or diagnostic agent(s) in order to encapsulate and/or entrap the agent(s) in the gel particles and nanostructures therein. It is believed that by first forming the gel without loading of agents and then subsequently loading (i.e., encapsulating and/or entrapping) the agent(s) into the self-assembled gel (in bulk or broken into particles thereof) it is possible to preserve the properties of the gel, as opposed to forming the gel in combination with the agent(s) in a single step.

Therapeutic, prophylactic, and/or diagnostic agents may be small molecules, proteins (including antibodies), peptides, sugars and polysaccharides, lipids and lipoproteins or lipopolysaccharides, or nucleic acids such as small interfering RNA, microRNA, PiRNA, ribozymes, and nucleotides encoding proteins or peptides.

These may have activity as anti-inflammatory agents, non-anti-inflammatory agents, steroids, anesthetics such as lidocaine or benzocaine, analgesics, anti-pyretic agents, anti-infectious agents such as antibacterial agents, anti-protozoal agents, antifungal agents, and antiviral agents, immunosuppressants, chemotherapeutics, growth factors, cytokines, or immunomodulatory molecules. Numerous drugs are available that can be delivered with these formulations. Additional agents include anthelmintic, anti-arrhythmic agents, anti-hypertensive agents, anticoagulants, antidepressants, agents for control of blood sugar, anti-epileptics, anti-gout agents, anti-malarials, anti-migraine agents, anti-muscarinic agents, anti-neoplastic agents, erectile dysfunction improvement agents, anxiolytic agents, sedatives, hypnotics, neuroleptics, blockers, cardiac inotropic agents, diuretics, histamine $H_1$ and $H_2$ receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, vitamins, minerals, and mixtures thereof.

Preferred compounds for delivery include immunomodulatory agents, such as immunosuppressants like tacrolimus, cyclosporine, and other calcineurin inhibitors, biological immunomodulatory agents such as cytokines such as GM-CSF, IL-22, and agonists and antagonists of immunomodulatory agents such as anti-TNF, anti-p19, anti-MADCAM, Janus kinase (JAK) inhibitors, regenerative agents such as EP4, erythropoietin, antibodies to treat arthritis such as tofacitinib, as well as anti-infective and chemotherapeutics.

In some embodiments, two or more agents, as described above, may be physically entrapped, encapsulated, and/or non-covalently associated with the nanostructures in the self-assembled gel. One agent may potentiate the efficacy of another encapsulated agent.

The therapeutic, prophylactic, and/or diagnostic agents may in general be encapsulated at a concentration between about 0.1 mg/mL and about 100 mg/mL, in certain instances at a concentration of between about 0.1 mg/mL and about 10 mg/mL, and in other instances at a concentration of between about 0.1 mg/mL and about 5 mg/mL, or ranges disclosed therein, in the self-assembled gels.

The gels can also contain a detectable label, such as, a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. These may be encapsulated within, dispersed within, or conjugated to the nanostructures in the self-assembled gel.

In some embodiment, the weight percent of the agent compared to the total weight of the agent and the gelator in the gel or gel particles is between about 0.1% and about 30%, preferably between about 0.5% and about 15%, and most preferably between about 2% and about 12%. In some embodiments, the agent is tacrolimus, and optionally the gelator is ascorbyl palmitate.

4. Gel Particles

With self-assembled gel compositions, typically no gravitational flow is observed upon inversion of a container at room temperature for at least 10 seconds, and in some cases, for about 1 hour, 3 hours, 1 day, 2 days, 3 days, one week or longer. A self-assembled gel is homogeneous and stable to inversion at room temperature, unlike heterogeneous materials that is a mixture of gelled regions (non-flowable) and non-gelled, liquid regions (flowable). A self-assembled gel is also different from liposome or micelle suspensions. Liposome or micelles suspensions are not self-supporting and can flow when the container is inverted.

In some embodiments, the self-assembled gel compositions have recoverable rheological properties, i.e., self-assembled gel is shear-thinning, suitable for injection, and recovers to a self-supporting state after cessation of a shear force. The self-supporting state generally features an elastic modulus of from 10 to 10,000 Pascal and greater than a viscous modulus. Due to non-covalent interactions for the assembly of gelators, a bulk gel may deform and be extruded under a shear force (e.g., during injection), and the gelators re-assemble upon cessation of shear forces to a self-supporting, stable-to-inversion state (e.g., elastic modulus G' greater than viscous modulus G").

For further formulation, the gel is formed into particles by homogenization, sonication, or otherwise dispersal in a suspension medium and further collected. In some embodiments, particles are nanoparticles having a hydrodynamic diameter between 100 nm and 990 nm, preferably between 500 nm and 900 nm, and the nanoparticles maintain at least 50, 60, 70 or 80% of the size in serum over a period of at least two hours. In other embodiments, particles are microparticles having a diameter ranging from 1 μm to a couple hundred millimeters. Particles can have sizes within the range of about 0.1-3000 microns, more preferably about 0.5-1000 microns, and larger particles and/or aggregates thereof can be optionally broken to reduce the size to a range of about 0.5-200 microns In some embodiments, the nanoparticles and/or microparticles have a minimum dimension of 2 nm or more, 50 nm or more, 100 nm or more, 150 nm or more, 200 nm or more, 250 nm or more, 300 nm or more, 350 nm or more, 500 nm or more, 1,000 nm or more, 5,000 nm or more, or 10,000 nm or more, and/or 10,000 nm or less, 5,000 nm or less, 1,000 nm or less, 500 nm or less, 400 nm or less, 350 nm or less, 300 nm or less, 250 nm or less, 200 nm or less, 150 nm or less, 100 nm or less, or 50 nm or less. The particles may aggregate into networks, and/or be in the form of a liquid crystal, emulsion, or other types of morphologies.

The gel compositions can be prepared for controlled release and/or degradation over a period of time. In some embodiments, the release kinetics of can be tuned by including one or more additional co-gelators, such as GRAS amphiphiles described above, which can be used to increase or decrease the rate of release of the agents encapsulated and/or entrapped within the nanostructures, such as fibers, of the gels. More typically, release is controlled through modifications of the pharmaceutical excipients, such as enteric or mucoadhesive coatings on the particles, gel capsule or tablet.

5. Gel Formulations

Self-assembled gel formulations may be prepared in dry powder formulations or liquid formulations. The gel are typically sterilized or sterile. For example, a sterile formulation can be prepared by first performing sterile filtration of gelators, as well as agents to be encapsulated, followed by processes of preparing the gels in an aseptic environment. Alternatively, all processing steps can be performed under non-sterile conditions, and then terminal sterilization (e.g., gamma or E-beam irradiation) can be applied to the resulting hydrogels or products thereof.

Dry formulations contain lyophilized self-assembled gel compositions where solvent is removed, resulting in xerogels. Xerogels can be in a powder form, which can be useful for maintaining sterility and activity of agents during storage and for processing into desired forms. As xerogels are solvent free, they can have improved shelf-life and can be relatively easily transported and stored. To lyophilize self-assembled gels, the gels can be frozen (e.g., at −80° C.) and vacuum-dried over a period of time to provide xerogels.

Alternatively, a dry formulation contains dry powder components of gelators, and one or more therapeutic agents, which are stored in separate containers, or mixed at specific ratios and stored. In some embodiments, suitable aqueous and organic solvents are included in additional containers. In some embodiments, dry powder components, one or more solvents, and instructions on procedures to mix and prepare assembled nano structures are included in a kit.

Liquid gel formulations contain self-assembled gel composition suspended in a liquid pharmaceutical carrier. In some forms, self-assembled gel is suspended or re-suspended in aqueous media for ease of administration and/or reaching a desired concentration for minimizing toxicity.

Particle properties may be modified prior to or after formulation, as discussed below.

Exemplary formulations contain tacrolimus as the agent. In some embodiments, the formulations contain ascorbyl palmitate as the gelator.

The weight percent of the agent (i.e., tacrolimus) compared to the total weight of the agent and the gelator in the gel or gel particles can be between about 0.1% and about 30%, preferably between about 0.5% and about 15%, and most preferably between about 2% and about 12%, such as about 11% or about 2%. In some embodiments, the formulations contain sodium starch glycolate as a disintegrant and mannitol as a filler. The weight percent of the gel particles in the formulations can be between about 2% and about 80%, preferably between about 5% and about 70%, and most preferably between about 10% and about 60% such as about 10% or about 60%. In some embodiments, the formulations are compressed into tablets or placed in capsules that are coated with an enteric polymer, such as EUDRAGIT® L 100-55.

III. Method of Making

1. Making a Self-Assembled Gel

Generally, a water-miscible organic solvent dissolves gelators to form a gelator solution. An aqueous medium (e.g., water, hypotonic solution, isotonic solution, or hypertonic solution) is added and mixed with the gelator solution. At appropriate volume ratios of the organic solvent and the aqueous solution, gelation begins as soon as the aqueous medium is mixed with the gelator solution. Over time, the gel becomes consistent. Gelation is deemed complete when the gel is self-supporting and stable to inversion at room temperature for at least 10 seconds, and in some cases, for about 10 minutes, 30 minutes, 1 day, 3 days, 1 week, 2 weeks, 3 weeks, or longer, i.e., not "runny" or flow due to gravity, and preferably having little to no precipitates and little to no aggregates therein. A self-assembled gel is homogeneous and stable to inversion, unlike heterogeneous materials that are a mix of gelled regions (non-flowable) and non-gelled, liquid regions (flowable).

Organic solvent(s) used in the gelation medium can be selected based on the solubility of gelators therein, its polarity, hydrophobicity, water-miscibility, and in some cases the acidity. Suitable organic solvents include water-miscible solvent, or solvent that has an appreciable water solubility (e.g., greater than 5 g/100 g water), e.g., DMSO, dipropylene glycol, propylene glycol, hexyl butyrate, glycerol, acetone, dimethylformamide (DMF), tetrahydrofuran, dioxane, acetonitrile, alcohol such as ethanol, methanol or isopropyl alcohol, as well as low molecular weight polyethylene glycol (e.g., 1 kDa PEG which melts at 37° C.). In other forms, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, N,N'-dimethyl formamide, ethanol, isopropyl alcohol, butyl alcohol, pentyl alcohol, tetrahydrofuran, xylene, mesitylene, and/or any combination thereof. Organic solvents for gelation include dimethyl sulfoxide (DMSO), dipropylene glycol, propylene glycol, hexyl butyrate, glycerol, acetone, dimethylformamide, tetrahydrofuran, dioxane, acetonitrile, ethanol, and methanol. Another class of organic solvents, fatty alcohols or long-chain alcohols, are usually high-molecular-weight, straight-chain primary alcohols, but can also range from as few as 4-6 carbons to as many as 22-26, derived from natural fats and oils. Some commercially important fatty alcohols are lauryl, stearyl, and oleyl alcohols. Some are unsaturated and some are branched.

The aqueous solvent is typically water which may be sterilized and selected from distilled water, de-ionized water, pure or ultrapure water. In some instances the aqueous solvent is an aqueous solution such as saline, other physiologically acceptable aqueous solutions containing salts and/or buffers, such as phosphate buffered saline (PBS), Ringer's solution, and isotonic sodium chloride, or any other aqueous solution acceptable for administration to a subject, such as an animal or human. The amounts of aqueous solvent, such as water, is typically based on the amounts of the organic solvent used wherein the selected total volume or weight percentage of organic solvent(s) determined the volume or weight percentage of the water or aqueous solution (e.g., if 30 v/v % of organic solvent then 70 v/v % water).

In some instances, the amount of an organic solvent is no more than 1:1, 1:2, 1:3, 1:4, 1:5, 1:6, 1:7, 1:8, 1:9, 1:10, or less in volume compared to the volume of an aqueous solution (e.g., water, aqueous buffer, aqueous salt solution, optionally containing one or more additional agents). That is, the volume amount of the organic solvent in the total amount of liquid as used in forming a homogeneous gel is generally less than about 50%, 33%, 25%, 20%, 17%, 14%, 12.5%, 11%, 10%, 9%, 8%, 7%, 6%, 5%, 4%, 3%, 2%, or 1% or less.

Gelation may require heating the gelation medium to temperatures ranging about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some embodiments, heating is carried out in the temperature range of about 60-80° C. In some embodiments, the heating is carried out at about 80° C.

In some instances, no heating is needed, or, if necessary, heating to about body temperature (37° C.) generates a homogeneous self-supporting gel that is stable to inversion. In other embodiments, the gelation medium is heated to complete dissolution, followed by cooling to about 37° C. or room temperature around 20° C.-25° C.

Gelation can take place with or without heating. When heated, gelation can take place as the heated gelation solution is cooled. Leaving the gel on a stable surface for about one to two hours at room temperature results in a consistent self-supporting gel. Self-supporting gel comprises orderly assembled micro- or nano-structures with minimal precipitates. This is generally confirmed using optical or electron microscopy.

In order to achieve a favorable particle size and size distribution it is necessary to first make a uniform solution of gelator. If a uniform solution is not achieved the gelator will not properly self-assemble and the formulation will have large amorphous chunks. As demonstrated by the examples, the tacrolimus and gelator are combined as solids, then the solvent such as an aqueous-organic solvent mixture, is added. Typical organic solvents include alcohols such as methanol and dimethyl sulfoxide (DMSO). The highest concentration of tacrolimus in solvent (methanol, MeOH) in the examples is 129 mg/mL, or 160 mM. The lowest tacrolimus level in the examples is 2.14 mg/mL, or 2.7 mM. The gelator concentration in solvent in the examples is fixed at 286 mg/mL, or 690 mM. The highest concentration of tacrolimus in the aqueous/organic gelator media in the examples is 43 mg/mL, or 53.3 mM. The gelator concentration in the aqueous/organic gelator media in the examples is fixed at 95 mg/mL, or 230 mM. The solution of gelator and drug is heated to insure complete dissolution, then cooled to form a gel. This is broken up to form particles small enough for injection. The gel and/or particles are washed to remove residue organic solvent. These are then suspended for injection or freeze or spray dried. The dried particles or gel can be stored in individual use vials or an oral dosing bottle or encapsulated in capsules or tablets.

2. Loading Self-Assembled Gel with Agent(s)

In preferred embodiments, the agent(s) may be physically entrapped, encapsulated, and/or non-covalently associated with the nanostructures of the self-assembled gels by first forming the gel and then suspending the gel in an aqueous medium, such as a buffer, where the gel is optionally first broken to form particles (i.e., nano- and/or microparticles). Preferably, the self-assembled gel formed is free of or substantially free of organic solvent(s). Subsequently, the resulting gel suspension, which may be a gel particle suspension, is mixed with a second solution or suspension containing one or more agent(s) described herein. Typically the second solution or suspension is a buffer solution containing agent(s). Mixing may be carried out by any appropriate means. Non-limiting mixing means include pipetting and/or vortexing. Mixing may be carried out at room temperature. In some instances, no heating is needed when mixing.

In some forms, the bulk self-assembled gel prior to agent(s) being loaded is first suspended in water, phosphate buffered saline, or other physiological saline, which is homogenized or sonicated to break up the bulk gel into particles which retain the fibrous nanostructures formed in the bulk gel. These particles may be collected, stored, purified, and reconstituted prior to loading of agent(s). Different types of gel particles may be loaded with different amounts or types of agents.

Suspension of the self-assembled gel in water, a phosphate buffered saline, or some other physiological saline or suspension of agent(s) in water, a phosphate buffered saline, or some other physiological saline may be carried out by stirring, agitation, vortexing, or any other suitable method.

The self-assembled gels demonstrate loading efficiencies of the one or more agents up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %. In some embodiments, the loading of the agent(s) in the self-assembled gels are about 1 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per mL of hydrogel. In certain embodiments, the loading of agents in the self-assembled gels is in the range of between about 100 and 1000 mg per mL of hydrogel when the loading amounts are greater than or equal to 50%.

3. Gel Purification

Distillation, filtration, dialysis, centrifugation, tangential flow filtration, evaporation, other solvent exchange techniques, vacuum drying, or lyophilization may be used in one or more repeated processes to remove organic solvent(s) and/or unencapsulated and/or unentrapped excess agent(s) or any other unencapsulated and/or unentrapped agents present from the gels to below the stated limit of pharmaceutical product requirements. Solvent removal and/or removal of unencapsulated and/or unentrapped agent(s) can be carried out on the gel directly following formation, following formation of the gel suspension, or after the agent(s) has been loaded into the gel suspension. Generally, a purification medium is one suitable for administration, such that the solvent of the gel is at least partially replaced with the purification medium.

4. Formulation of Suspensions for Oral Administration or Instillation

In some instances, the formulation is distributed or packaged in a liquid form (e.g., suspension) for oral administration, for administration as an enema, or administration by instillation into a body cavity or lumen. Alternatively, formulations for non-injectable administration can be packaged as a solid, obtained, for example, by lyophilization of a suitable liquid formulation. The solid can be reconstituted with an appropriate carrier or diluent prior to administration.

Solutions and dispersions of the nanoparticles and/or microparticles can be prepared in water or another solvent or dispersing medium suitably mixed with one or more pharmaceutically acceptable excipients including, but not limited to, surfactants, dispersants, emulsifiers, pH modifying agents, and combination thereof.

The formulation is typically buffered to a pH of 3-8 for administration upon reconstitution. Suitable buffers are well known by those skilled in the art and some examples of useful buffers are acetate, borate, carbonate, citrate, and phosphate buffers.

Solutions, suspensions, or emulsions for administration may also contain one or more tonicity agents to adjust the isotonic range of the formulation. Suitable tonicity agents are well known in the art. Examples include glycerin, mannitol, sorbitol, sodium chloride, and other electrolytes.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles and/or microparticles.

5. Gelatin Capsules and Tablets

Tablets and inserts/suppositories can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations are prepared using pharmaceutically acceptable carriers including but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Optional pharmaceutically acceptable excipients include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and powdered sugar. The usual diluents include inert powdered substances such as starches, powdered cellulose, especially crystalline and microcrystalline cellulose, sugars such as fructose, mannitol and sucrose, grain flours, and similar edible powders. Typical diluents include, for example, various types of starch, lactose, mannitol, kaolin, calcium phosphate or sulfate, inorganic salts such as sodium chloride, and powdered sugar. Powdered cellulose derivatives are also useful.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin, and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

A lubricant can be used in a tablet formulation to prevent the tablet and punches from sticking in the die to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross-linked polymers, such as cross-linked PVP (POLYPLASDONE® XL from GAF Chemical Corp.).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; vitamin E, tocopherol and its salts; sulfites such as sodium metabisulphite; cysteine and its derivatives; citric acid; propyl gallate, and butylated hydroxyanisole (BHA).

In the preferred embodiment, size 9 capsules (approximately 2.7 mm×8.40 mm, giving them a surface area of 71.25 mm$^2$) are used to encapsulate the formulation, e.g., microfibers of the gel. These are dip coated with an enteric coating solution, causing an increase in capsule mass by about 3 mg. This yields a coating area density of 42 μg/mm$^2$. The size 9 capsules can be filled with about 20 mg of solid material. The amount of microfiber added depends on the drug loading and the target dose. Usually between about 2 and 10 mg (10-50% total capsule fill) of microfiber is added to each capsule, with the balance being sodium starch glycolate added as a disintegrant at 0.8-1.6 mg (4-8% of total capsule fill) and the balance as mannitol, which acts as bulking agent that also helps with rehydration (8-17 mg, 40-85% total capsule fill).

In some embodiment, the weight percent of the gel particles in the tablet or capsule formulations (with excipients) is between about 2% and about 80%, preferably between about 5% and about 70%, and most preferably between about 10% and about 60%. In some embodiments, the excipients include sodium starch glycolate (as a disintegrant) and mannitol (as a filler).

6. Formation into Vaginal or Rectal Inserts or Suppositories

Vaginal or rectal inserts or suppositories are typically formed by the same techniques as tablets, with additional excipient for comfort once inserted, such as increased amounts of inserts. The size and shape are selected based on the route of administration. These shapes, sizes, and excipients are well known to those in the pharmaceutical compounding art.

7. Enteric, Delayed or Pulsatile Release Formulations and Blended Formulations

A number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

Coatings can be applied to the particles, tablets, capsules, or inserts to modify release and to increase residence time at the site of delivery.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine from the clinical studies.

Coatings may be formed with a different ratio of water soluble polymer, water insoluble polymers and/or pH dependent polymers, with or without water insoluble/water soluble non-polymeric excipient, to produce the desired release profile. The coating is either performed on dosage form (matrix or simple) which includes, but are not limited to, tablets (compressed with or without coated beads), capsules (with or without coated beads), beads, particle compositions, and "ingredient as is" formulated as, but not limited to, suspension form or as a sprinkle dosage form.

Additionally, the coating material may contain conventional carriers such as plasticizers, pigments, colorants, glidants, stabilization agents, pore formers and surfactants.

In a preferred embodiment, lyophilized tacrolimus-loaded microfibers are adsorbed onto microcrystalline cellulose beads (60-250 μm mesh, or as large as 1,000 μm mesh) using a dry layering or suspension layering process. The microbeads are then coated by a fluidized bed coating process. Preferred coatings include pH responsive enteric coating, sustained released coating, and controlled release coating. In some embodiments, multi-layered coatings can be applied. The coated microbeads can be administered as a solid oral dosage form by loading them into a capsule or table. Alternatively, the coated microbeads can be suspended in water, buffer or other media and delivered as a liquid dosage form. Other buffering agents and excipients may be added to the liquid dosage form.

Enteric Coatings

The particles, tablets, capsules, or inserts may be coated to delay release to after the particles have passed through the acidic environment of the stomach. These materials are usually referred to as enteric coatings. For example, enteric polymers become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon.

Exemplary enteric polymers include polymethacrylates and derivatives thereof, such as ethyl methacrylate-methacrylic acid copolymer and those sold under the tradename EUDRAGIT®, naturally occurring cellulosic polymers (e.g., cellulose acetate succinate, cellulose acetate phthalate, hydroxy propyl methyl cellulose phthalate, and hydroxy propyl methyl cellulose acetate succinate) and other polysaccharides (e.g., sodium alignate, pectin, chitosan) or semi-synthetic or synthetic derivatives thereof, poly(2-vinylpyridine-co-styrene), polyvinyl acetate phthalate, shellac, fatty acids (e.g., stearic acid), waxes, plastics, and plant fibers.

Exemplary gastric resistant natural polymers include, but are not limited to, pectin and pectin-like polymers which typically consist mainly of galacturonic acid and galacturonic acid methyl ester units forming linear polysaccharide chains. Typically these polysaccharides are rich in galacturonic acid, rhamnose, arabinose and galactose, for example the polygalacturonans, rhamnogalacturonans and some arabinans, galactans and arabinogalactans. These are normally classified according to the degree of esterification. In high (methyl) ester ("HM") pectin, a relatively high portion of the carboxyl groups occur as methyl esters, and the remaining carboxylic acid groups are in the form of the free acid or as its ammonium, potassium, calcium or sodium salt. Useful properties may vary with the degree of esterification and with the degree of polymerization.

Pectin, in which less than 50% of the carboxyl acid units occur as the methyl ester, is normally referred to as low (methyl) ester or LM-pectin. In general, low ester pectin is obtained from high ester pectin by treatment at mild acidic or alkaline conditions. Amidated pectin is obtained from high ester pectin when ammonia is used in the alkaline deesterification process. In this type of pectin some of the remaining carboxylic acid groups have been transformed into the acid amide. The useful properties of amidated pectin may vary with the proportion of ester and amide units and with the degree of polymerization.

Synthetic enteric polymers include, but are not limited to, acrylic acid polymers and copolymers, preferably formed from acrylic acid, methacrylic acid, methyl acrylate, ethyl acrylate, methyl methacrylate and/or ethyl methacrylate, and methacrylic resins that are commercially available under the tradename EUDRAGIT® (Rohm Pharma; Westerstadt, Germany), including EUDRAGIT® L30 D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGIT® NE, RL and RS (water-insoluble polymers having different degrees of permeability and expandability).

The enteric coating is generally present in an amount less than about 10% by weight of the composition (e.g., gel particles, tablets, or capsules), preferably from about 2 to about 8% by weight of the composition.

The dosage units may be coated with the delayed release polymer coating using conventional techniques, e.g., using a conventional coating pan, an airless spray technique, or fluidized bed coating equipment (with or without a Wurster insert). See Pharmaceutical Dosage Forms: Tablets, Eds. Lieberman et al. (New York: Marcel Dekker, Inc., 1989), and Ansel et al., Pharmaceutical Dosage Forms and Drug Delivery Systems, 6th Ed. (Media, PA: Williams & Wilkins, 1995) for detailed information concerning materials, equipment and processes for preparing tablets and delayed release dosage forms.

Immediate Release/Extended Release Drug/Particle Blends

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Extended Release Dosage Forms

The extended release formulations are generally prepared as diffusion or osmotic systems, for example, as described in "Remington—The Science and Practice of Pharmacy" (20th Ed., Lippincott Williams & Wilkins, Baltimore, MD, 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, CARBOPOL® 934, and polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms can be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours, and similar edible powders. Typical diluents include, for example, various types of starch, lactose, mannitol, kaolin, calcium phosphate or sulfate, inorganic salts such as sodium chloride, and powdered sugar. Powdered cellulose derivatives are also useful. Typical tablet binders include substances such as starch, gelatin, and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose, and waxes can also serve as binders. A lubricant can be used in a tablet formulation to prevent the tablet and punches from sticking in the die. The lubricant is chosen from such slippery solids as talc, magnesium and calcium stearate, stearic acid, and hydrogenated vegetable oils.

Extended release tablets or inserts containing wax materials are generally prepared using methods known in the art such as a direct blend method, a congealing method, and an aqueous dispersion method. In a congealing method, the drug is mixed with a wax material and either spray-congealed or congealed and screened and processed.

Delayed Release Dosage Forms

Delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate, and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGIT® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil, and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release Formulations

By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design, e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than three tablets, dosage forms housing more than three tablets can be utilized.

Alternatively, each dosage unit in the capsule may comprise a plurality of drug-containing beads, granules or particles. Drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. Drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In another embodiment, the individual dosage units are compacted in a single tablet, and may represent integral but discrete segments thereof (e.g., layers), or may be present as a simple admixture. For example, drug-containing beads, granules or particles with different drug release profiles (e.g., immediate and delayed release profiles) can be compressed together into a single tablet using conventional tableting means.

In a further alternative embodiment, a dosage form is provided that comprises an inner drug-containing core and at least one drug-containing layer surrounding the inner core. An outer layer of this dosage form contains an initial, immediate release dose of the drug. For dosage forms mimicking twice daily dosing, the dosage form has an outer layer that releases drug substantially immediately following oral administration and an inner core having a polymeric-coating that preferably releases the active agent approximately 3 hours to less than 14 hours following ingestion of the dosage unit. For dosage forms mimicking three times daily dosing, the dosage form has an outer layer that releases drug substantially immediately following oral administration, an inner core that preferably releases drug at least 5 hours to 18 hours following oral administration and a layer interposed between the inner core and outer layer that preferably releases drug approximately 3 hours to 10 hours following ingestion of the dosage form. The inner core of the dosage form mimicking three times daily dosing may be formulated as compressed delayed release beads or granules.

Alternatively, for dosage forms mimicking three times daily dosing, the dosage form has an outer layer and an inner layer free of drug. The outer layer releases drug substantially immediately following oral administration, and completely surrounds the inner layer. The inner layer surrounds both the second and third doses and preferably prevents release of these doses for approximately 3 hours to 10 hours following oral administration. Once released, the second dose is immediately available while the third dose is formulated as delayed release beads or granules such that release of the third dose is effected approximately 2 hours to 8 hours thereafter effectively resulting in release of the third dose at least 5 hours to approximately 18 hours following ingestion of the dosage form. The second and third doses may be formulated by admixing immediate release and delayed release beads, granules or particles and compressing the admixture to form a second and third dose-containing core followed by coating the core with a polymer coating to achieve the desired three times daily dosing profile.

In still another embodiment, a dosage form is provided which comprises a coated core-type delivery system wherein the outer layer is comprised of an immediate release dosage unit containing an active agent, such that the active agent therein is immediately released following oral administration; an intermediate layer there under which surrounds a core; and a core which is comprised of immediate release beads or granules and delayed release beads or granules, such that the second dose is provided by the immediate release beads or granules and the third dose is provided by the delayed release beads or granules.

Film-Forming Polymers for Coating Capsules

The film-forming composition can be used to prepare soft or hard shell gelatin capsules which can encapsulate a liquid or semi-solid fill material or a solid tablet (e.g., SOFT-LET®) containing an active agent and one or more pharmaceutically acceptable excipients. Alternatively, the composition can be administered as a liquid with an active agent dissolved or dispersed in the composition. Exemplary film-forming natural polymers include, but are not limited to, gelatin and gelatin-like polymers. In a preferred embodiment, the film-forming natural polymer is gelatin. A number of other gelatin-like polymers are available commercially. The film-forming natural polymer is present in an amount from about 20 to about 40% by weight of the composition, preferably from about 25 to about 40% by weight of the composition.

The film-forming composition can be used to prepare soft or hard capsules using techniques well known in the art. For example, soft capsules are typically produced using a rotary die encapsulation process. Fill formulations are fed into the encapsulation machine by gravity.

The capsule shell can contain one or more plasticizers selected from the group consisting of glycerin, sorbitol, sorbitans, maltitol, glycerol, polyethylene glycol, polyalcohols with 3 to 6 carbon atoms, citric acid, citric acid esters, triethyl citrate and combinations thereof. In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include titanium dioxide, zinc oxide, calcium carbonate, and combinations thereof. Colorants can be used for marketing and product identification/differentiation purposes. Suitable colorants include synthetic and natural dyes and combinations thereof.

Humectants can be used to suppress the water activity of the soft gel. Suitable humectants include glycerin and sorbitol, which are often components of the plasticizer composition. Due to the low water activity of dried, properly stored soft gels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Mucoadhesive Particles and Methods of Manufacturing

In general terms, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., van der Waals interactions) and stronger specific interactions, which include hydrogen bonds. The hydrophilic functional groups responsible for forming hydrogen bonds are the hydroxyl (—OH) and the carboxylic groups (—COOH).

Suitable polymers that can be used to form bioadhesive coatings include soluble and insoluble, biodegradable and non-biodegradable polymers. These can be hydrogels or thermoplastics, homopolymers, copolymers or blends, natural or synthetic. Two classes of polymers have appeared to show useful bioadhesive properties: hydrophilic polymers and hydrogels. In the large class of hydrophilic polymers, those containing carboxylic groups (e.g., poly(acrylic acid)) exhibit the best bioadhesive properties. In other studies, the most promising polymers were: sodium alginate, carboxymethylcellulose, hydroxymethylcellulose and methylcellulose. Some of these materials are water-soluble, while others are hydrogels.

Rapidly bioerodible polymers such as poly(lactide-co-glycolide), polyanhydrides, and polyorthoesters, whose carboxylic groups are exposed on the external surface as their smooth surface erodes, are excellent candidates for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, polysaccharides, such as cellulose, dextrans, poly(hyaluronic acid), and polymers of acrylic and methacrylic esters and alginic acid. Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, and copolymers thereof. Synthetically modified natural polymers include alkyl celluloses, hydroxyalkyl celluloses, cellulose ethers, cellulose esters, and nitrocelluloses. The attachment of any positively charged ligand, such as polyethyleneimine or polylysine, may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge. Any ligand with a high binding affinity for mucin could also be covalently linked and be expected to influence the binding of microspheres to the gut. The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the microspheres. The polyamino chains would increase bioadhesion by means of chain entanglement in mucin strands as well as by increased carboxylic charge.

8. Sterilization

A sterile formulation is prepared by first performing sterile filtration of the process solutions (e.g., agent and gelator solutions), followed by gel preparation, suspension, purification and lyophilization under aseptic processing conditions. Alternatively, all processing steps can be performed under non-sterile conditions, and then terminal sterilization (e.g., gamma or E-beam irradiation) can be applied to the lyophilized hydrogel product. Sterile solution for resuspension can also be prepared using similar methods.

IV. Methods of Use

The self-assembled gel, its suspension formulation, particle formulation, or capsules, tablets, inserts, or suppositories made from the particles is administered to deliver an effective dosage of the therapeutic, prophylactic and/or diagnostic agent(s) to diagnose, alleviate, prevent, or treat one or more symptoms of a disease or disorder. Administration can be orally, vaginally, rectally (enema), or as insert, or by instillation into a body lumen such as the bladder.

Figure 2:
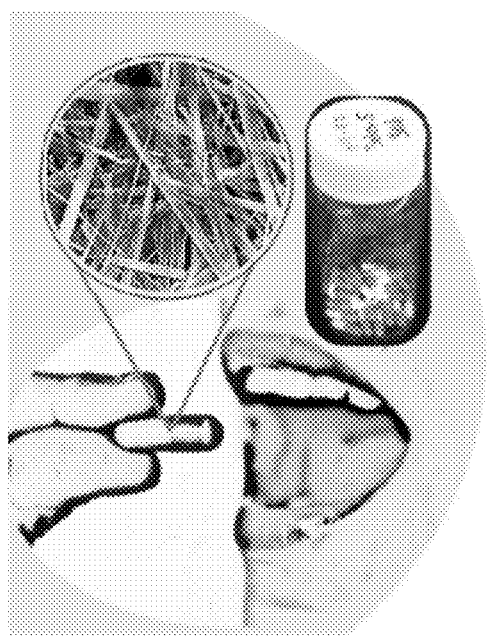
FIG. 2 is a schematic of the drug loaded gel displaying characteristic nanostructures in inset, encapsulated into an enteric coated capsule, and being orally administered, to a human.

FIG. 2 is a schematic of the drug loaded gel displaying characteristic nanostructures in inset, encapsulated into an enteric coated capsule, being orally administered, to a human.

Delivered agent(s) can be controllably released from the gel compositions in response to stimuli for targeted release. In the absence of stimuli, the agent is released in a sustained manner with little to no burst release. For example, encapsulated agents can be gradually released over a period of time (e.g., hours, one day, two days, three days, a week, a month, or more). Depending on the parameters, release can be delayed or extended from minutes to days when gel compositions are administered under physiological conditions (a pH of about 7.4 and a temperature of about 37° C.). The rate of release may be increased in regions with decreased pH or elevated enzyme activity, such as in tumors, infected sites, and areas of inflammation.

In the preferred embodiment, a drug such as tacrolimus is loaded into ascorbyl palmitate gels orally administered as a suspension, tablet or capsule. In the most preferred embodiment, the particles and/or tablet or capsule are enteric coated to enable GI site-specific dissolution and release. These formulations can be used to treat active (symptomatic) autoimmune or inflammatory diseases and/or prevent their recurrence.

Routes of Administration

The formulations are administered orally, rectally or vaginally, or into any body lumen using instillation or insertion as of a suppository or insert. The formulation can be swallowed if administered in the form of a suspension, tablet or capsule. The formulation is administered by syringe, catheter, or instillation syringe if administered by instillation.

While in most cases administration is non-invasive, the formulation may be administered during surgery or minimally invasive procedures such as laparoscopy.

Diseases or Disorders to be Treated

The drugs to be administered are determined by the disease or disorders to be treated. The pharmacokinetics are expected to be different for drugs administered in the claimed formulations as compared to convention tablets or capsules not including the hydrogels. The pharmacokinetics will also be impacted by the route of administration and whether or not coatings including enteric coatings, controlled or sustained release film forming polymer coatings and/or mucoadhesive coatings have been applied.

The formulations can be used to administer drug locally, regionally or systemically.

Representative disorders and diseases to be treated include cancer, inflammation and infection, as well as metabolic diseases and autoimmune diseases. In the preferred embodiment, the drug is an anti-inflammatory to treat a gastrointestinal disorder such as irritable bowel syndrome, ulcerative colitis, hyperactive bowel, and hemorrhoids, and/or an infection such as those that cause ulcers, venereal disease, and yeast overgrowth.

Dosages

The effective dosage is readily determined from the known pharmacokinetics of the therapeutic, prophylactic or diagnostic agents, modified in view of the kinetics measured in vitro and in animal and human clinical trials, as is routinely done by those skilled in the art. The terms "sufficient" and "effective", as used interchangeably herein, refer to an amount (e.g. mass, volume, dosage, concentration, and/or time period) needed to achieve one or more desired result(s) or alleviation of one or more symptoms of the disease or disorder.

The present invention will be further understood by reference to the following non-limiting examples.

Example 1: Preparation of Tacrolimus-Loaded Ascorbyl Palmitate Hydrogel Suspensions with Tunable Drug Loading Materials and Methods
Representative Formulation Process for Tacrolimus-Loaded Ascorbyl Palmitate Hydrogel Suspensions:

Ascorbyl palmitate (AP) (400 mg) and tacrolimus (Tac) (120 mg) were weighed into a 20 mL scintillation vial. The solids were dissolved in methanol (1.4 mL). Millipore water (2.8 mL) was added and the suspension heated in a hot water bath at 80° C. for 6 minutes with stirring. The vial was removed from the hot water bath and cooled in a room temperature water bath for 30 minutes. The vial was removed from the water bath and left undisturbed at room temperature for an additional 18 hours. The resulting hydrogel was suspended in water (35 mL) and centrifuged (5,000 RPM, 4° C., 10 minutes). The supernatant containing impurities, such as excess drug and methanol, was discarded. The gel pellet was resuspended again in water (35 mL). The centrifugation and resuspension process was repeated three times for gel purification. The purified gel pellet was resuspended in water, typically between 5 and 50 mL depending on desired final tacrolimus concentration. After resuspension, the ascorbyl palmitate concentration can be 0.1-80 mg/mL and the tacrolimus concentration can be 0.1-25 mg/mL.

Assessment of Loading and Encapsulation Efficiency:

Aliquots of suspended hydrogel (1 mL) were transferred to centrifuge tubes and centrifuged (20,000 RCF, 4° C., 10 minutes). The supernatant was removed by pipette and diluted in 1% citric acid in methanol. The residual pellet was dissolved in DMSO (1 mL) and diluted in 1% citric acid in methanol. The tacrolimus and ascorbyl palmitate content in the supernatant and residual pellet were assayed by HPLC to assess encapsulated tacrolimus and free (i.e., unencapsulated) tacrolimus content of the formulation. The tacrolimus loading (wt/wt %) can be tuned by adjusting the amount of tacrolimus added during the formulation process (Table 1).

Results

The tacrolimus loading (wt/wt %) can be tuned by adjusting the amount of tacrolimus added during the formulation process (Table 1).

TABLE 1

Tacrolimus hydrogels and the effects of tacrolimus feed concentration on tacrolimus loading in ascorbyl palmitate hydrogels

| Formulation | Theoretical Loading* | Experimental Drug Loading** | Encapsulation Percentage*** | Encapsulation Efficiency**** |
|---|---|---|---|---|
| $Tac_{(180\ mg)}:AP_{(400\ mg)}$ | 31% | 29.7% | 96.8% | 95.8% |
| $Tac_{(120mg)}:AP_{(400\ mg)}$ | 23% | 22.4% | 94.9% | 97.1% |
| $Tac_{(60mg)}:AP_{(400\ mg)}$ | 13% | 11.2% | 96.9% | 86.2% |
| $Tac_{(18\ mg)}:AP_{(400\ mg)}$ | 4.3% | 2.0% | 86.8% | 46.5% |
| $Tac_{(12\ mg)}:AP_{(400\ mg)}$ | 2.9% | 0.8% | 74.6% | 26.9% |
| $Tac_{(9\ mg)}:AP_{(400\ mg)}$ | 2.2% | 0.4% | 85.8% | 17.7% |
| $Tac_{(6\ mg)}:AP_{(400\ mg)}$ | 1.5% | 0.2% | >98% | 13.3% |
| $Tac_{(3\ mg)}:AP_{(400\ mg)}$ | 0.7% | 0.1% | >98% | 12.9% |

*Theoretical drug loading = tac added (mg)/(tac added (mg) + AP added (mg))
**Experimental drug loading = tac measured in pellet (mg)/(tac measured in pellet (mg) + AP measured in pellet (mg))
***Encapsulation percentage = tac measured in pellet (mg)/(tac measured in pellet (mg) + tac measured in supernatant (mg))
****Encapsulation efficiency = experimental drug loading/theoretical drug loading These studies are based on combining the tacrolimus and gelator as solids, and then adding the solvent. The highest concentration of tacrolimus in solvent (methanol, MeOH) that was tested was 129 mg/mL, or 160 mM, although this is not the upper limit. The lowest tacrolimus level formulated was 2.14 mg/mL, or 2.7 mM, although it is not the lowest possible level. The gelator concentration in solvent was fixed at 286 mg/mL, or 690 mM.

The highest concentration of tacrolimus in the aqueous/organic gelator media was 43 mg/mL, or 53.3 mM. The gelator concentration in the aqueous/organic gelator media is fixed at 95 mg/mL, or 230 mM.

In order to achieve a favorable particle size and size distribution it is necessary to first make a uniform solution in gelator. If a uniform solution is not achieved, the gelator will not properly self-assemble and the formulation will have large amorphous chunks.

Example 2. Preparation of Enteric Coated Size 9 Capsules Containing Tacrolimus Loaded Ascorbyl Palmitate Microfibers Materials and Methods Frozen tacrolimus-loaded ascorbyl palmitate hydrogel suspension ($Tac_{(60\ mg)}:AP_{(400\ mg)}$) was lyophilized to give a fluffy white powder. The gel concentration, or conversely the water volume, was found to be an important factor that affects the flowability and texture of the final dried powder, with more dilute conditions being optimal. The tacrolimus and ascorbyl palmitate content of the powder was confirmed by HPLC analysis. The powder was then blended with sodium starch glycolate as a disintegrant and mannitol as a capsule filler to create a capsule fill formulation. Typically, the disintegrant is incorporated at a weight ratio of 0-8% and the capsule filler is incorporated at a weight ratio of 0-90%. For example, $Tac_{(60\ mg)}:AP_{(400\ mg)}$ powder (1.5793 g) was combined with sodium starch glycolate (1.2318 g) and mannitol (12.6255 g), which resulted in a final weight ratio of 10.2%, 8.0%, and 81.8%, respectively. The solid powder components were mixed thoroughly by shaking to create a uniform capsule fill formulation. Fill formulation uniformity was confirmed by HPLC analysis of 6 separate samples (RSD Tac=6.29%, RSD AP=5.73%).

Capsule Filling for Tacrolimus-Loaded Ascorbyl Palmitate Fill Formulation

Size 9 hydroxypropyl methylcellulose (HPMC) capsules (40 capsules) were loaded into a Multi Capsule Filler (TORPAC®). Size 9 capsules were used for proof of concept, but this process is amenable to human sized capsules such as size 5 to size 000. Tacrolimus-loaded ascorbyl palmitate fill formulation (850 mg) was loaded onto the Multi Capsule Filler, yielding 40 capsules filled with approximately 20 mg of the fill formulation. Empty capsules had an average weight of 8.5±0.7 mg. Filled capsules had an average weight of 28.3±1.2 mg. The amount of filled powder had an average weight of 19.8±1.4 mg.

Capsule Dip Coating Process for Size 9 HPMC Capsules

A coating solution was prepared by dissolving EUDRAGIT® L 100-55 polymer (11.49 g) in a solution of acetone (74.2 mL), isopropanol (113.5 mL), water (7.8 mL), and triethyl citrate (1.15 g). Capsules were loaded in groups of 6 into a Size 9 Coating Holder (Braintree Scientific, Inc.). Capsules were partially submerged (≥50%) into the coating solution for 30 seconds and then allowed to air-dry for 20 minutes. Each capsule was flipped end-over-end and dipped again to ensure both ends were coated. This process was carried out a total of three times. Complete and even coating was confirmed by submerging 20 randomly selected capsules for two hours in pH 1.6 fasted-state simulated gastric fluid (FaSSGF) and then one hour in pH 6.5 fasted-state simulated intestinal fluid (FaSSIF). Capsule disintegration was monitored over time until all 20 had dissolved (Table 2). A batch is deemed a success when >80% of the capsules remain intact during the two-hour FaSSGF incubation and rupture within 10 minutes of FaSSIF incubation. The coated capsules had an average weight of 30.4±1.4 leading to an average coating weight of 2.1±1.8 mg.

Results

The disintegration data in simulated gastric and simulated intestinal fluids are shown in Table 2.

Microscopy of a tacrolimus-loaded microfiber suspension and a tacrolimus-loaded microfiber suspension that has been lyophilized and blended with mannitol and sodium starch glycolate for capsule filling show that the size and shape of tac-loaded microfibers are not affected by the lyophilization and capsule filling process.

TABLE 2

Number of capsules remaining intact after incubation in FaSSGF and FaSSIF

| | Time (min) | | | | | |
|---|---|---|---|---|---|---|
| | 30 | 45 | 75 | 120 | 125 | 130 |
| FaSSGF pH 1.6 | 20/20 | 20/20 | 18/20 | 18/20 | — | — |
| FaSSIF pH 6.5 | — | — | — | — | 10/20 | 0/20 |

Example 3. Preparation of Tacrolimus Loaded Ascorbyl Stearate Hydrogel Suspensions Ascorbyl stearate is more hydrophobic than ascorbyl palmitate and therefore forms more tightly packed microfiber structures. As a result, the microfibers are better at excluding water and less prone to aqueous hydrolysis and enzymatic degradation. Ascorbyl stearate can be used to slow the degradation profile of the microfibers structures, which can be used to adjust drug release rate.

Materials and Methods

Representative Formulation Process for Tacrolimus-Loaded Ascorbyl Stearate Hydrogel Suspensions Ascorbyl stearate (AS) (400 mg) and tacrolimus (Tac) (120 mg) were weighed into a 20 mL scintillation vial. The solids were dissolved in methanol (1.4 mL). Millipore water (2.8 mL) was added and the suspension heated in a hot water bath at 80° C. for 6 minutes with stirring. The vial was removed from the hot water bath and cooled in a room temperature water bath for 30 minutes. The vial was removed from the water bath and left undisturbed at room temperature for an additional 18 hours. The resulting hydrogel was suspended in water (35 mL) and centrifuged (5,000 RPM, 4° C., 10 minutes). The supernatant containing impurities, such as excess drug and methanol, was discarded. The gel pellet was resuspended again in water (35 mL). The centrifugation and resuspension process was repeated three times for gel purification. The purified gel pellet was resuspended in water, typically between 5 and 50 mL depending on desired final tacrolimus concentration.

The degradation experiment for ascorbyl stearate ("AS") and ascorbyl palmitate ("AP") hydrogel suspensions were performed via incubation in PBS at 37° C. with shaking, in the presence of lipase from *Thermomyces lanuginosus* (Sigma-Aldrich) at 100 μg/mL. Time-dependent release of AP and AS from the hydrogel was quantified by HPLC to determine the degradation kinetics.

Results

Figure 3:
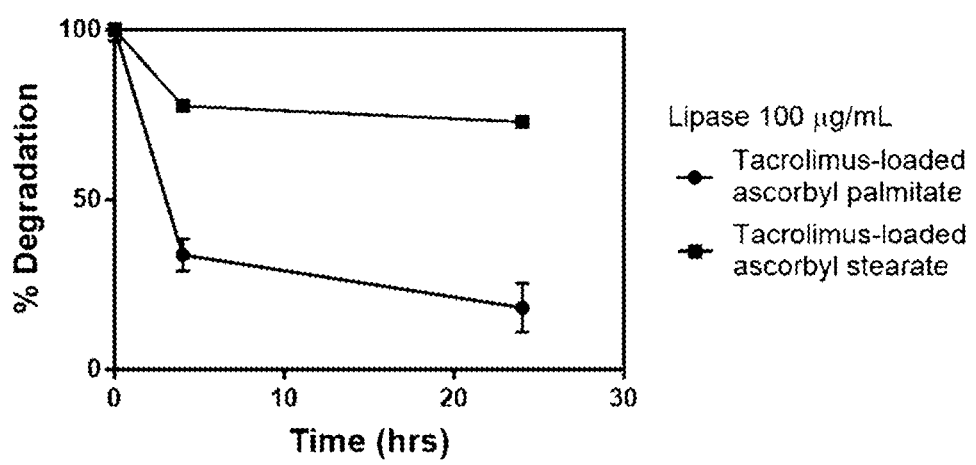
FIG. 3 is a graph of gel degradation for ascorbyl stearate ("AS") and ascorbyl palmitate ("AP") measured as % AP or % AS over time (hours) for gel exposed to lipase at 100 μg/mL.

Samples were assessed for drug loading and encapsulation percentage as described in example one and found to be 22.5% and 97.2%, respectively. After resuspension, the ascorbyl stearate concentration can be 0.1-80 mg/mL and the tacrolimus concentration can be 0.1-25 mg/mL. FIG. 3 shows the slower enzymatic degradation profile for ascorbyl stearate microfibers compared to ascorbyl palmitate microfibers.

Example 4. Controlling Microfiber Size and Morphology with Organic Solvent

The gelation process outlined in Examples 1 and 3 uses methanol as an organic solvent, but several other water-miscible organic solvents can be used in place of methanol. For example, dimethyl sulfoxide, ethanol, and isopropanol have been used successfully to prepare self-assembled microstructures amenable to drug encapsulation and controlled release. The criteria for selection of solvent systems are the size and uniformity of particles, the encapsulation efficiency, and the ease of manufacturing and purification. Methanol provides high encapsulation efficiency, uniform microfiber distribution, and a simple manufacturing protocol. Particle morphologies can be modified by changing the organic solvent used during microparticle preparation.

Materials and Methods

Representative Formulation Process for Ascorbyl Palmitate Hydrogel Suspensions:

Ascorbyl palmitate (100 mg) was weighed into 4 separate 7 mL glass vials. The ascorbyl palmitate was dissolved in 350 µL of DMSO, methanol, ethanol, or isopropanol. Millipore water (700 µL) was added to the 4 vials, each containing ascorbyl palmitate dissolved in a different solvent. The vials were heated to 80° C. for 6 minutes and then cooled in a room temperature water bath for 18 hours. The microparticle were resuspended in water (12 mL) and analyzed by laser diffraction and light microscopy.

Results

Table 3 lists the particle sizes observed for microstructures prepared with DMSO, methanol, ethanol, and isopropanol. Particles sizes were measured using a Mastersizer 3000 laser diffraction instrument (Malvern Panalytical, Ltd.).

TABLE 3

Particle size distributions for microparticles using different organic solvents during preparation

| Solvent | Dx(10) (µm) | Dx(50) (µm) | Dx(90) (µm) |
|---|---|---|---|
| DMSO | 0.715 | 9.68 | 26.9 |
| Methanol | 2.31 | 8.71 | 37.6 |
| Ethanol | 13.5 | 46.2 | 110 |
| Isopropanol | 12.5 | 49.9 | 148 25 |

Example 5: Enzyme Responsiveness and Drug Release Properties of Tacrolimus-Loaded Microfiber Suspensions Materials and Methods Capsules were tested for the effect of lipase on release of tacrolimus. The gel degradation experiment was performed by incubating tacrolimus hydrogel suspension (10 mg/mL AP) in PBS at 37° C. with shaking in the presence of lipase from *Thermomyces lanuginosus* (Sigma-Aldrich) at 100 µg/mL, 30 µg/mL, 10 µg/mL, and 0 µg/mL. AP concentration was measured by HPLC to determine the degradation kinetics.

Tacrolimus release was performed the same as gel degradation but using an 8-10 kDa dialysis bag and 2 mg/mL lipase; tacrolimus release was measured after two weeks using HPLC.

Results

Figure 4:
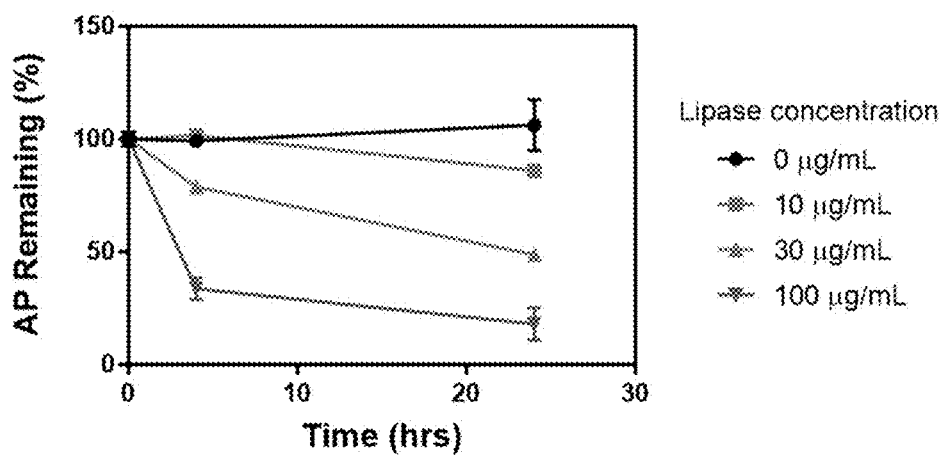
FIG. 4 is a graph of gel degradation measured as % tacrolimus (AP) remaining over time (hours) for gel exposed to lipase: 0, 10, 30 and 100 μg/mL.
Figure 5:
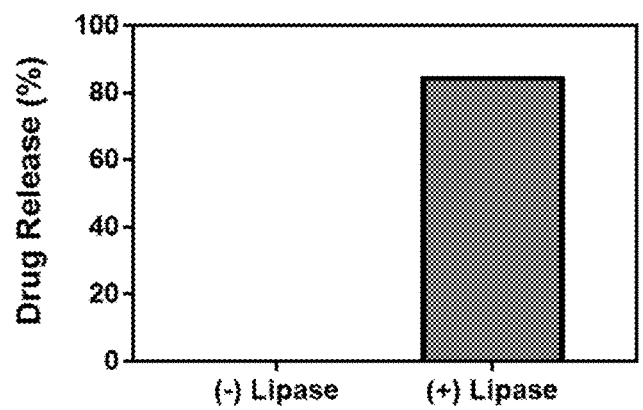
FIG. 5 is a graph of tacrolimus release with and without lipase.

FIG. 4 is a graph of gel degradation measured as % tacrolimus (AP) remaining over time (hours) for gel exposed to lipase: 0, 10, 30 and 100 µg/ml. FIG. 5 is a graph of tacrolimus release with and without lipase.

The results demonstrate that tacrolimus-loaded drug formulations are stable in phosphate buffered saline (PBS) but degrade in the presence of lipase, an enzyme associated with inflammation. The degradation rate is proportional to the level of enzyme present. Up to 85% tacrolimus release occurs from lipase-degraded gels while no release occurs from non-degraded gels.

Example 6: In Vivo Test of Formulations Hydrogel Encapsulated Tacrolimus

Capsule and Hydrogel Encapsulated Tacrolimus Suspension in a Rat Indomethacin-Induced Model of Inflammatory Bowel Disease Materials and Methods Formulations of tacrolimus prepared as described above were tested using the indomethacin-induced model of inflammatory bowel disease. Briefly, female Lewis rats (~175-200 g body weight) were randomized into groups and, with the exception of the "healthy" rat group (Group 1), received a single subcutaneous injection of indomethacin on study days 0 and 1 (9 mg/kg indomethacin and 1 ml/kg of 5% sodium bicarbonate in sterile water). On study days 0 through 4, indomethacin-induced rats were administered a single daily dose of one of the following treatments: Group 2—"vehicle" (0.5 mL oral gavage of water), Group 3—"Tacrolimus suspension" (1 mg/kg tacrolimus suspended in a water vehicle and administered through a duodenal-implanted catheter), Group 4—"hydrogel encapsulated tacrolimus suspension" ($Tac_{(60\ mg)}:AP_{(400\ mg)}$, 1 mg/kg tacrolimus as prepared in Example 1 and administered through a duodenal-implanted catheter), Group 5—hydrogel encapsulated tacrolimus capsule ($Tac_{(60\ mg)}:AP_{(400\ mg)}$, 1 mg/kg tacrolimus dosage as prepared in Example 2 and administered by oral gavage, Group 6—generic Prograf suspension (1 mg/kg tacrolimus suspended in water and administered by oral gavage.

On study day 5, blood pharmacokinetic (PK) samples were draw at 0, 0.5, 2 and 8 hours after the final doses were administered. Animals were then sacrificed and 10 cm of the jejunum was excised, weighed, and scored as follows:

0=Normal.
0.5=Very Minimal thickening, multifocal in area at risk.
1=Minimal thickening, fairly diffuse in area at risk.
2=Mild to moderate small intestinal/mesenteric thickening throughout area at risk.
3=Moderate thickening with 1 or more definite adhesions that would be easy to separate.
4=Marked thickening with numerous hard to separate adhesions.
5=Severe intestinal lesion resulting in death.

Intestinal tissue was then homogenized and extracted to quantify tacrolimus.

Statistical analysis of the data was performed using a one-way ANOVA with a Tukey post hoc test. Statistical significance relative to the vehicle control is indicated by an asterisk (*) while statistical significance compared to the Tacrolimus suspension is indicated by a pound sign (#). Statistical significance is indicated as follows: */#p<0.05; /##p<0.01; */###p<0.001; ****/####p<0.0001.

Results

Figure 6A:
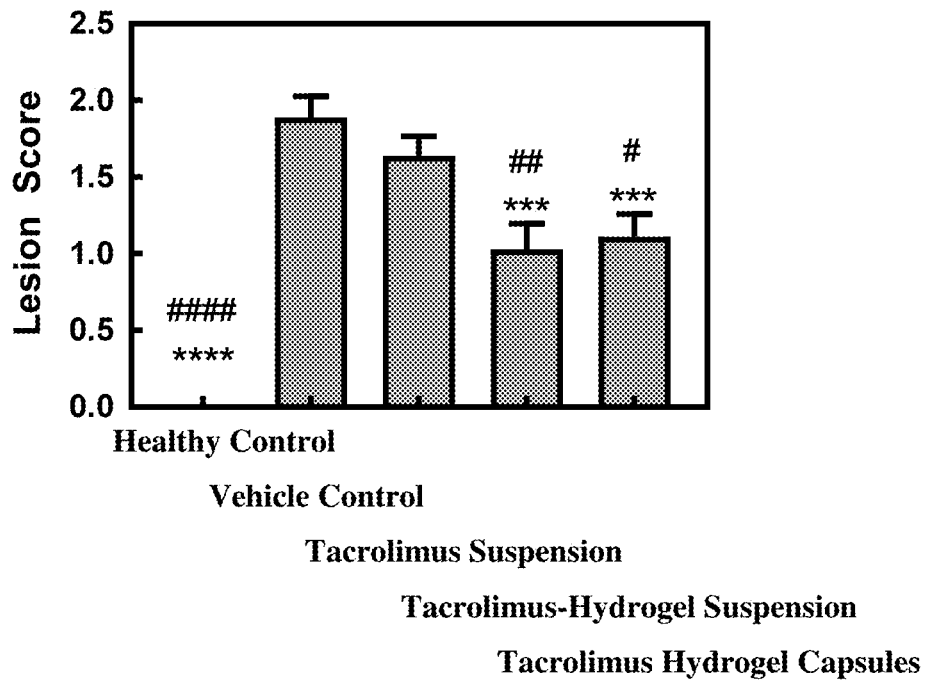
FIG. 6A is a graph of the jejunum lesion scores versus formulation.

Jejunum lesion scores for each group are shown in FIG. 6A. Both the hydrogel encapsulated tacrolimus suspension and hydrogel encapsulated tacrolimus capsule result in a statistical reduction in lesion score compared to the vehicle only treatment, demonstrating the ability of these formulations to treat small intestinal inflammation in rats. Conversely, the tacrolimus suspension that lacks an inflammation-targeting gelator does not improve the lesion score compared to the vehicle treatment. Furthermore, the hydrogel encapsulated tacrolimus suspension and hydrogel encapsulated tacrolimus capsule groups both have statistically lower lesion scores compared to the tacrolimus suspension, thereby demonstrating the benefit of the inflammation-targeting gelator.

Figure 6B:
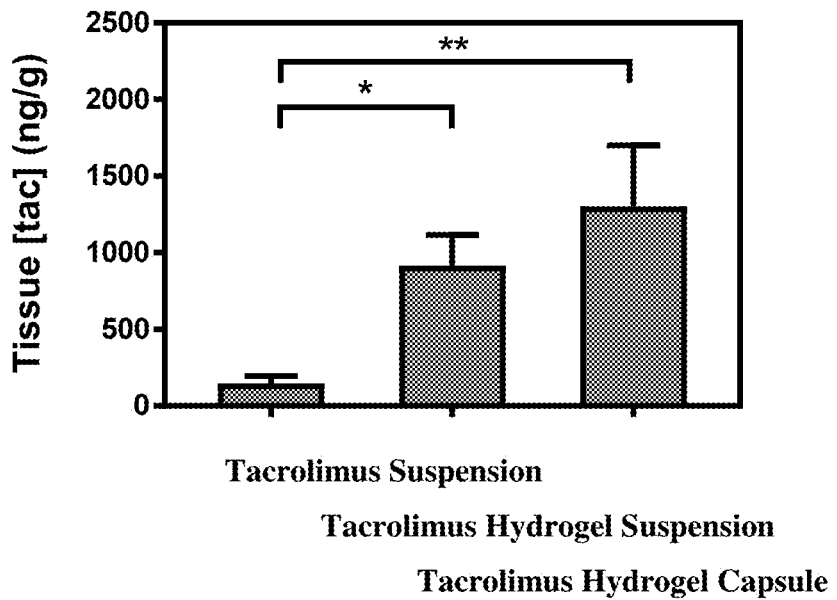
FIG. 6B is a graph of the jejunum tacrolimus concentration versus formulation.

Tissue concentrations of tacrolimus for each group are shown in FIG. 6B. In comparison to the tacrolimus suspension, both hydrogel encapsulated tacrolimus suspension and hydrogel encapsulated tacrolimus capsule result in statistically higher tacrolimus tissue levels due to the inflammation-targeting gelator.

Figure 6C:
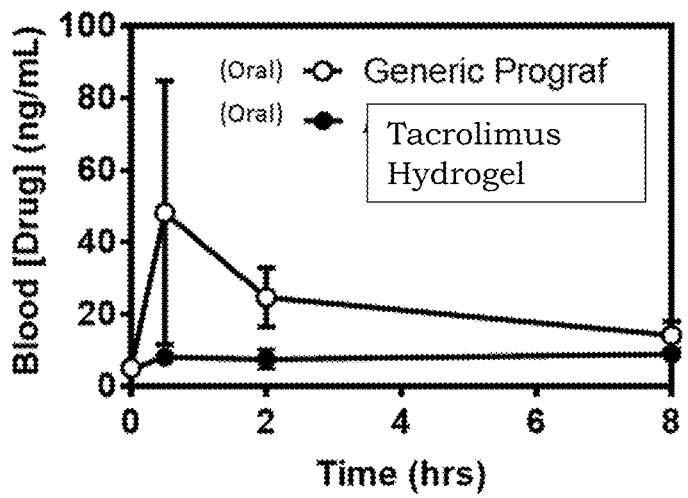
FIG. 6C is a graph of blood tacrolimus concentration versus time for generic prograf (tacrolimus) and hydrogel encapsulated tacrolimus.

Blood concentrations of tacrolimus versus time for the hydrogel encapsulated tacrolimus capsule and generic Prograf are shown in FIG. 6C. The hydrogel encapsulated tacrolimus capsule results in a lower tacrolimus area under the curve (AUC) of the blood concentration vs. time graph and a lower maximum tacrolimus blood concentration ($C_{max}$) compared to the orally dosed generic Prograf.

Example 7. Preparation of Hydrogel Encapsulated Tacrolimus Capsules Containing Tacrolimus-Loaded Ascorbyl Palmitate Microfibers, In Vitro Disintegration Testing and In Vivo Testing in a Rat Indomethacin-Induced Model of Inflammatory Bowel Disease Materials and Methods Tacrolimus-loaded ascorbyl palmitate hydrogel suspension ($Tac_{(18\ mg)}$:$AP_{(400\ mg)}$) was prepared as outlined in Example 1 and lyophilized. The tacrolimus and ascorbyl palmitate content of the powder was confirmed by HPLC analysis. The $Tac_{(18\ mg)}$:$AP_{(400\ mg)}$ powder (2.1356 g) was then combined with sodium starch glycolate (0.2840 g) and mannitol (1.1383 g), which resulted in a final weight ratio of 60%, 8.0%, and 32%, respectively. The solid powder components were mixed thoroughly to create a uniform capsule fill formulation. Fill formulation uniformity was confirmed by HPLC analysis of 4 separate samples (RSD Tac=4.03%, RSD AP=3.82%).

Capsule Filling and Coating

Size 9 hydroxypropylmethylcellulose (HPMC) capsules (40 capsules) were loaded into a Multi Capsule Filler (TORPAC®). Tacrolimus-loaded ascorbyl palmitate fill formulation (720 mg) was loaded onto the Multi Capsule Filler, yielding 40 capsules filled with approximately 16 mg of the fill formulation. Empty capsules had an average weight of 8.5±0.7 mg. Filled capsules had an average weight of 24.4±1.5 mg. The amount of filled powder had an average weight of 15.9±1.6 mg. Capsules were then coated with EUDRAGIT® L 100-55 polymer as described in Example 2. The coated capsules had an average weight of 28.0±1.0 leading to an average coating weight of 3.6±1.8 mg. Disintegration testing was performed as outlined in Example 2.

In Vivo Test of Tacrolimus-Hydrogel Capsules in the Rat Indomethacin Model

Tacrolimus hydrogel capsules were tested in the rat-indomethacin-induced IBD model as described in Example 6.

Results

The disintegration data in simulated gastric and simulated intestinal fluids are shown in Table 4. Three capsules ruptured after fifteen minutes incubation in FaSSGF, but the remainder stayed intact throughout the two-hour incubation. After two hours, the capsules were submerged in FaSSIF and ruptured within five minutes. Microscopy of a tacrolimus-loaded microfiber suspension and a tacrolimus-loaded microfiber suspension that has been lyophilized and blended with mannitol and sodium starch glycolate for capsule filling show that the size and shape of tac-loaded microfibers are not affected by the lyophilization and capsule filling process.

TABLE 4

Number of Tacrolimus Hydrogel capsules remaining intact after incubation in FaSSGF and FaSSIF

| | Time (min) | | | | | |
|---|---|---|---|---|---|---|
| | 30 | 45 | 75 | 120 | 125 | 130 |
| FaSSGF pH 1.6 | 17/20 | 17/20 | 17/20 | 17/20 | — | — |
| FaSSIF pH 6.5 | — | — | — | — | 0/20 | 0/20 |

Figure 7:
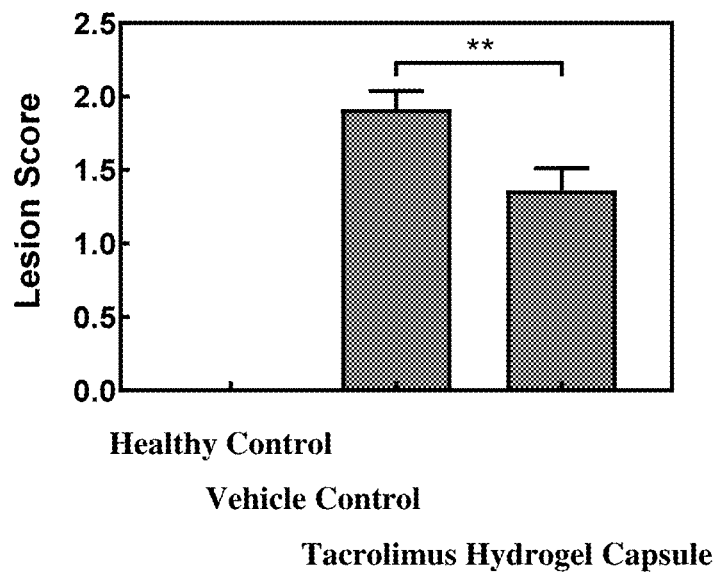
FIG. 7 is a graph of the jejunum lesion scores for the hydrogel-encapsulated tacrolimus capsule formulation.

Results from Tacrolimus hydrogel tests in the rat indomethacin model are shown in FIG. 7. Treatment with Tacrolimus hydrogel capsules resulted in a statistically significant reduction in jejunum lesion scores in comparison to the vehicle control. In comparison to hydrogel encapsulated tacrolimus capsules, this data demonstrates that the lower loaded tacrolimus formulation with less excipient content is also efficacious at the same 1 mg/kg dosing.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

We claim:

1. A formulation for administration to the gastrointestinal tract comprising particles, the particles comprising:
   ascorbyl palmitate self-assembled to form a nanostructured gel through non-covalent interactions between molecules of ascorbyl palmitate; and
   a therapeutically effective amount of tacrolimus, wherein the tacrolimus is entrapped or encapsulated in the nanostructured gel;
   wherein the nanostructured gel comprises a drug loading of between about 2% and about 30% by weight of tacrolimus.

2. The formulation of claim 1, wherein the particles are formed by heating then cooling a mixture of ascorbyl palmitate, tacrolimus, an organic solvent, and water wherein the ascorbyl palmitate self-assembles to form a nanostructured gel through non-covalent interactions between the ascorbyl palmitate molecules, wherein the tacrolimus is entrapped or encapsulated in the nanostructured gel.

3. The formulation of claim 1, wherein the particles are suspended in an aqueous liquid.

4. The formulation of claim 1, further comprising IL-22.

5. The formulation of claim 1, wherein the particles are disposed in a tablet, capsule, suppository or insert that is coated with a polymer to control release of the tacrolimus from the tablet, capsule, suppository or insert.

6. The formulation of claim 5, wherein the polymer is an enteric polymer.

7. The formulation of claim 5, wherein the polymer is a film forming polymer.

8. The formulation of claim 5, comprising a mucoadhesive polymer coating.

9. The formulation of claim 3, further comprising IL-22.

10. The formulation of claim 1, wherein the particles are selected from nanoparticles, microparticles, spheres, sheets, fibers, and tapes.

11. The formulation of claim 1, wherein the particles are suspended in a pharmaceutically acceptable carrier.

12. The formulation of claim 1, wherein particles are lyophilized or dried into a powder.

13. The formulation of claim 10, wherein the particles are nanoparticles.

14. The formulation of claim 13, wherein the nanoparticles have a length or width of 50-500 nanometers.

15. The formulation of claim 13, wherein the nanoparticles have a length or width of 1-25 microns.

* * * * *